US012391964B2

(12) United States Patent
Yamaguchi et al.

(10) Patent No.: US 12,391,964 B2
(45) Date of Patent: Aug. 19, 2025

(54) METHOD FOR PRODUCING POLYISOPRENOID, VECTOR, TRANSFORMED PLANT, METHOD FOR PRODUCING PNEUMATIC TIRE, AND METHOD FOR PRODUCING RUBBER PRODUCT

(71) Applicants: SUMITOMO RUBBER INDUSTRIES, LTD., Kobe (JP); TOHOKU UNIVERSITY, Sendai (JP); KANAZAWA UNIVERSITY, Kanazawa (JP)

(72) Inventors: Haruhiko Yamaguchi, Kobe (JP); Yukino Inoue, Kobe (JP); Kazuhisa Fushihara, Kobe (JP); Seiji Takahashi, Sendai (JP); Toru Nakayama, Sendai (JP); Satoshi Yamashita, Kanazawa (JP)

(73) Assignees: SUMITOMO RUBBER INDUSTRIES, LTD., Kobe (JP); TOHOKU UNIVERSITY, Kobe (JP); KANAZAWA UNIVERSITY, Kanazawa (JP)

(*) Notice: Subject to any disclaimer, the term of this patent is extended or adjusted under 35 U.S.C. 154(b) by 266 days.

(21) Appl. No.: 17/799,027

(22) PCT Filed: Feb. 22, 2021

(86) PCT No.: PCT/JP2021/006637
§ 371 (c)(1),
(2) Date: Aug. 11, 2022

(87) PCT Pub. No.: WO2021/177074
PCT Pub. Date: Sep. 10, 2021

(65) Prior Publication Data
US 2023/0167465 A1 Jun. 1, 2023

(30) Foreign Application Priority Data
Mar. 5, 2020 (WO) .................. PCT/JP2020/009416

(51) Int. Cl.
*C12P 5/00* (2006.01)
*C12N 9/10* (2006.01)
*C12N 15/82* (2006.01)

(52) U.S. Cl.
CPC ............ *C12P 5/007* (2013.01); *C12N 9/1085* (2013.01); *C12N 15/8242* (2013.01); *C12Y 205/01028* (2013.01); *C12Y 205/01089* (2013.01)

(58) Field of Classification Search
None
See application file for complete search history.

(56) References Cited

U.S. PATENT DOCUMENTS

| 7,335,815 | B2 * | 2/2008 | Boronat | ............... C12N 9/1085 |
| | | | | 536/23.6 |
| 2016/0244774 | A1 * | 8/2016 | Inoue | .................. C12N 15/8223 |
| 2017/0051313 | A1 | 2/2017 | Inoue et al. | |
| 2018/0171364 | A1 | 6/2018 | Yamaguchi et al. | |
| 2019/0376093 | A1 | 12/2019 | Sakurai et al. | |

FOREIGN PATENT DOCUMENTS

| EP | 3 059 318 A1 | 8/2016 |
| JP | 2013-162776 A | 8/2013 |
| JP | 2014-212706 A | 11/2014 |
| JP | 2014239664 A * | 12/2014 |
| JP | 2016-59313 A | 4/2016 |
| JP | 2016-154458 A | 9/2016 |
| JP | 2017-12058 A | 1/2017 |
| JP | 2020-36560 A | 3/2020 |
| WO | WO 2017/002818 A1 | 1/2017 |
| WO | WO 2018/116726 A1 | 6/2018 |

OTHER PUBLICATIONS

Montoro, Pascal, et al. "Expression of the HEV2. 1 gene promoter in transgenic Hevea brasiliensis." Plant cell, tissue and organ culture 94 (2008): 55-63. (Year: 2008).*

Priya, P et al. "Molecular cloning and characterization of the rubber elongation factor gene and its promoter sequence from rubber tree (Hevea brasiliensis): A gene involved in rubber biosynthesis." Plant science : an international journal of experimental plant biology vol. 171,4 (2006): 470-80. (Year: 2006).*

Feller, Antje, et al. "Evolutionary and comparative analysis of MYB and bHLH plant transcription factors." The plant journal 66.1 (2011): 94-116. (Year: 2011).*

Tata, Sandeep Kumar, et al. "Laticifer tissue-specific activation of the Hevea SRPP promoter in Taraxacum brevicorniculatum and its regulation by light, tapping and cold stress." Industrial Crops and Products 40 (2012): 219-224. (Year: 2012).*

(Continued)

*Primary Examiner* — Amjad Abraham
*Assistant Examiner* — Kelsey L McWilliams
(74) *Attorney, Agent, or Firm* — Birch, Stewart, Kolasch & Birch, LLP

(57) ABSTRACT

Provided is a method for producing a polyisoprenoid, which makes it possible to synthesize in vitro a polyisoprenoid having an unprecedented structure, such as a 100% cis-polyisoprenoid or a polyisoprenoid containing an allylic diphosphate derivative as an initiating terminal. Also provided is a method for producing a polyisoprenoid in vitro, which employs a gene coding for a neryl diphosphate synthase and rubber particles bound to a protein encoded by the gene, or a method for producing a polyisoprenoid, which includes introducing into a plant a vector in which a gene coding for a neryl diphosphate synthase is linked to a promoter having a promoter activity that drives laticifer-specific gene expression to express a protein encoded by the gene specifically in laticifers.

4 Claims, 7 Drawing Sheets

Specification includes a Sequence Listing.

(56) References Cited

OTHER PUBLICATIONS

Rodríguez-Concepción, Manuel, ed. Plant Isoprenoids: Methods and Protocols. Humana Press, 2014. (Year: 2014).*

Kwon, M., E-Jg Kwon, and D. K. Ro. "cis-Prenyltransferase and polymer analysis from a natural rubber perspective." Methods in Enzymology. vol. 576. Academic Press, 2016. 121-145. (Year: 2016).*

Schilmiller, Anthony L., et al. "Monoterpenes in the glandular trichomes of tomato are synthesized from a neryl diphosphate precursor rather than geranyl diphosphate." Proceedings of the National Academy of Sciences 106.26 (2009): 10865-10870. (Year: 2009).*

English translation of JP 2014212706 A, published Nov. 17, 2014 (Year: 2014).*

Salehi, Maryam, et al. "Natural rubber-producing sources, systems, and perspectives for breeding and biotechnology studies of Taraxacum kok-saghyz." Industrial crops and products 170 (2021): 113667. (Year: 2021).*

Vranová, Eva, Diana Coman, and Wilhelm Gruissem. "Structure and dynamics of the isoprenoid pathway network." Molecular plant 5.2 (2012): 318-333. (Year: 2012).*

Rodríguez-Concepción, Manuel, ed. Plant Isoprenoids: Methods and Protocols. Humana Press, 2014. Gawarecka and Swiezewska; Chapter 9, pp. 135-142 (Year: 2014).*

Schilmiller et al., "Monoterpenes in the glandular trichomes of tomato are synthesized from a neryl0 diphosphate precursor rather than geranyl diphosphate," Proceedings of the National Academy of Sciences, vol. 106, No. 26, Jun. 30, 2009, pp. 10865-10870.

International Search Report, issued in PCT/JP2021/006637, PCT/ISA/210, dated Apr. 13, 2021.

Written Opinion of the International Searching Authority, issued in PCT/JP2021/006637, PCT/ISA/237, dated Apr. 13, 2021.

* cited by examiner

```
                                            Helix3 region
UDP (M. luteus B-P 26CPT) (SEQ ID NO: 29)  75  TEWS DNY PGDF NTF--LPE--IEKN KY TTI IDD PDETKKAVLE  129
UPPS (Escherichia coli) (SEQ ID NO: 30)    71  SRWN AQI FVWA DSE---VVS--HRHN RL III PSRENSRLQER KK  125
Srt2 (Yeast CPT) (SEQ ID NO: 31)          131  FN  FN DTH FTVK DEFAKRA DYKDPLYGSKI IV DSL SPEMRKK KK  180
HDS (Human CPT) (SEQ ID NO: 32)            80  EK  S S PG  ARQKFSRL-MEE E-K QKHG CI VL LHL PLDLQEI AQ  137
```

Fig. 5

1 : Example 1
2 : Example 2

METHOD FOR PRODUCING POLYISOPRENOID, VECTOR, TRANSFORMED PLANT, METHOD FOR PRODUCING PNEUMATIC TIRE, AND METHOD FOR PRODUCING RUBBER PRODUCT

CROSS-REFERENCE TO RELATED APPLICATIONS

This application is the National Phase of PCT International Application No. PCT/JP2021/006637, filed on Feb. 22, 2021, which claims priority under 35 U.S.C. § 119 (a) to Patent Application No. PCT/JP2020/009416, filed in Japan on Mar. 5, 2020, all of which are hereby expressly incorporated by reference into the present application.

REFERENCE TO SEQUENCE LISTING

This application includes an electronically submitted sequence listing in .txt format. The .txt file contains a sequence listing entitled "5051-0552PUS1 ST25.txt" created on Nov. 26, 2024, and is 34,215 bytes in size. The sequence listing contained in this .txt file is part of the specification and is hereby incorporated by reference herein in its entirety.

TECHNICAL FIELD

The present disclosure relates to a method for producing a polyisoprenoid, a vector, a transgenic plant, a method for producing a pneumatic tire, and a method for producing a rubber product.

BACKGROUND ART

At present, natural rubber (a type of polyisoprenoid) for use in industrial rubber products may be obtained by cultivating rubber-producing plants, such as para rubber tree (Hevea brasiliensis) of the family Euphorbiaceae or Indian rubber tree (Ficus elastica) of the family Moraceae. Such natural rubber is a polyisoprenoid in which isoprene units are linked in a cis configuration. However, natural rubber synthesized in plants has a cis-linked backbone but contains trans-farnesyl diphosphate (E, E-FPP) as an initiating terminal (@-terminal), and therefore has a substantially cis configuration as a trans configuration is partially incorporated. Thus, no natural rubber in which all isoprene units are linked in a cis configuration has ever existed.

In nature, neryl diphosphate synthase is known to bind dimethylallyl diphosphate (DMAPP) and isopentenyl diphosphate (IPP) in a cis configuration. However, since this enzyme allows for elongation of an isoprenoid chain only having up to 10 carbon atoms, it can synthesize a short 100% cis-isoprenoid chain, but is unable to synthesize a high molecular weight polyisoprenoid.

Moreover, in the case of polyisoprene rubber, which is a synthetic rubber obtained by chemically binding isoprene units, it is also difficult to control the polymerization reaction to give a complete cis configuration, and thus a trans-bond will be incorporated during the polymerization reaction.

SUMMARY OF DISCLOSURE

Technical Problem

As described above, no 100% cis-polyisoprenoid has been able to be synthesized either in nature or in chemical synthesis, and there has been no 100% cis-polyisoprenoid in which all isoprene units are linked in a cis configuration.

Moreover, polyisoprenoids generally contain farnesyl diphosphate (FPP) as an initiating terminal. Although there have been examples of synthesis of isoprenoids containing another allylic diphosphate derivative as an initiating terminal, they have a molecular weight of 10,000 or smaller.

The present disclosure aims to solve the above problem and provide a method for producing a polyisoprenoid, which makes it possible to synthesize in vitro a polyisoprenoid having an unprecedented structure, such as a 100% cis-polyisoprenoid or a polyisoprenoid having an unprecedented terminal.

The present disclosure also aims to solve the above problem and provide a vector that can be introduced into a plant using genetic recombination techniques to enhance polyisoprenoid production. Further objects are to provide a transgenic plant into which the vector has been introduced and to provide a method for enhancing production of a cis-isoprenoid or polyisoprenoid in a plant by introducing the vector into the plant.

Solution to Problem

The present disclosure relates to a method for producing a polyisoprenoid, the method including binding a protein expressed from a gene coding for a neryl diphosphate synthase to rubber particles in vitro. This disclosure is hereinafter called the first aspect of the present disclosure and also referred to as the first disclosure.

Preferably, the polyisoprenoid is a 100% cis-polyisoprenoid.

Preferably, the gene coding for a neryl diphosphate synthase is derived from a plant.

Preferably, the gene coding for a neryl diphosphate synthase is derived from tomato.

Preferably, the gene coding for a neryl diphosphate synthase includes the following DNA [1] or [2]:

[1] a DNA having the nucleotide sequence represented by SEQ ID NO: 7; or

[2] a DNA which hybridizes under stringent conditions to a DNA having a nucleotide sequence complementary to the nucleotide sequence represented by SEQ ID NO: 7, and which codes for a protein having an enzyme activity that catalyzes a reaction to synthesize neryl diphosphate using isopentenyl diphosphate and dimethylallyl diphosphate as substrates.

Preferably, the neryl diphosphate synthase is a mutant protein obtained by replacing the helix 3 region by the helix 3 region of a cis-prenyltransferase capable of producing an isoprenoid chain having 35 or greater carbon atoms.

Preferably, an allylic diphosphate derivative is used as a starting substrate, and the neryl diphosphate synthase is a mutant protein obtained by replacing the helix 3 region by the helix 3 region of a cis-prenyltransferase capable of producing an isoprenoid chain having 35 or greater carbon atoms.

Preferably, the binding includes performing protein synthesis in the presence of both rubber particles and a cell-free protein synthesis solution containing an mRNA coding for a neryl diphosphate synthase to bind the neryl diphosphate synthase to the rubber particles.

Preferably, the cell-free protein synthesis solution contains a germ extract.

Preferably, the germ extract is derived from wheat.

Preferably, the rubber particles are present at a concentration of 5 to 50 g/L in the cell-free protein synthesis solution.

The first disclosure also relates to a method for producing a pneumatic tire, the method including:
kneading a polyisoprenoid produced by the method for producing a polyisoprenoid according to the first disclosure with an additive to obtain a kneaded mixture;
building a green tire from the kneaded mixture; and
vulcanizing the green tire.

The first disclosure also relates to a method for producing a rubber product, the method including:
kneading a polyisoprenoid produced by the method for producing a polyisoprenoid according to the first disclosure with an additive to obtain a kneaded mixture;
forming a raw rubber product from the kneaded mixture; and
vulcanizing the raw rubber product.

The present disclosure also relates to a vector, including:
a promoter having a promoter activity that drives laticifer-specific gene expression; and
a gene coding for a neryl diphosphate synthase functionally linked to the promoter. This disclosure is hereinafter called the second aspect of the present disclosure and also referred to as the second disclosure.

Preferably, the promoter having a promoter activity that drives laticifer-specific gene expression is at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

The second disclosure also relates to a transgenic plant into which any of the above-defined vectors has been introduced.

The second disclosure also relates to a method for enhancing cis-isoprenoid production in a plant by introducing any of the above-defined vectors into the plant.

The second disclosure also relates to a method for enhancing polyisoprenoid production in a plant by introducing any of the above-defined vectors into the plant.

The second disclosure also relates to a method for producing a pneumatic tire, the method including:
kneading a polyisoprenoid produced by a transgenic plant with an additive to obtain a kneaded mixture, the transgenic plant being produced by introducing any of the above-defined vectors into a plant;
building a green tire from the kneaded mixture; and
vulcanizing the green tire.

The second disclosure also relates to a method for producing a rubber product, the method including:
kneading a polyisoprenoid produced by a transgenic plant with an additive to obtain a kneaded mixture, the transgenic plant being produced by introducing any of the above-defined vectors into a plant;
forming a raw rubber product from the kneaded mixture; and
vulcanizing the raw rubber product.

Advantageous Effects of Disclosure

The method for producing a polyisoprenoid according to the first disclosure includes binding a protein expressed from a gene coding for a neryl diphosphate synthase to rubber particles in vitro. Thus, by binding a neryl diphosphate synthase to rubber particles, it is possible to synthesize polyisoprenoids including a polyisoprenoid having an unprecedented structure such as a 100% cis-polyisoprenoid in the rubber particles, and therefore it is possible to efficiently produce polyisoprenoids in a reaction vessel (e.g., a test tube or industrial plant).

The method for producing a pneumatic tire of the first disclosure includes: kneading a polyisoprenoid produced by the method for producing a polyisoprenoid of the first disclosure with an additive to obtain a kneaded mixture; building a green tire from the kneaded mixture; and vulcanizing the green tire. With this method, which produces a pneumatic tire from a polyisoprenoid obtained by a highly efficient polyisoprenoid production method, it is possible to use plant resources effectively to produce environmentally friendly pneumatic tires.

The method for producing a rubber product of the first disclosure includes: kneading a polyisoprenoid produced by the method for producing a polyisoprenoid of the first disclosure with an additive to obtain a kneaded mixture; forming a raw rubber product from the kneaded mixture; and vulcanizing the raw rubber product. With this method, which produces a rubber product from a polyisoprenoid obtained by a highly efficient polyisoprenoid production method, it is possible to use plant resources effectively to produce environmentally friendly rubber products.

The vector of the second disclosure includes: a promoter having a promoter activity that drives laticifer-specific gene expression; and a gene coding for a neryl diphosphate synthase functionally linked to the promoter. By introducing the vector into a plant, the gene coding for a protein involved in polyisoprenoid biosynthesis in the vector can be expressed specifically in laticifers, thereby enhancing cis-isoprenoid or polyisoprenoid production in the plant.

The method for producing a pneumatic tire of the second disclosure includes kneading a polyisoprenoid produced by a transgenic plant with an additive to obtain a kneaded mixture, the transgenic plant being produced by introducing the vector of the second disclosure into a plant; building a green tire from the kneaded mixture; and vulcanizing the green tire. With this method, which produces a pneumatic tire from a polyisoprenoid produced by a transgenic plant with an enhanced polyisoprenoid production, it is possible to use plant resources effectively to produce environmentally friendly pneumatic tires.

The method for producing a rubber product of the second disclosure includes kneading a polyisoprenoid produced by a transgenic plant with an additive to obtain a kneaded mixture, the transgenic plant being produced by introducing the vector of the second disclosure into a plant; forming a raw rubber product from the kneaded mixture; and vulcanizing the raw rubber product. With this method, which produces a pneumatic tire from a polyisoprenoid produced by a transgenic plant with an enhanced polyisoprenoid production, it is possible to use plant resources effectively to produce environmentally friendly rubber products.

BRIEF DESCRIPTION OF DRAWINGS

FIG. 3 (SEQ ID NOS: 2, 8, 12 and 19, respectively) is an outline diagram illustrating the results of multiple sequence alignment of the amino acid sequences of the neryl diphosphate synthases used in EXAMPLES.

FIG. 4 (SEQ ID NOS: 25-28) is an outline diagram illustrating the results of multiple sequence alignment of the amino acid sequences of the neryl diphosphate synthases used in EXAMPLES.

FIG. 5 (SEQ ID NO: 29-32) is an outline diagram illustrating the results of multiple sequence alignment of cis-prenyltransferases derived from various organisms, each capable of producing an isoprenoid chain having 35 or greater carbon atoms.

DESCRIPTION OF EMBODIMENTS

Figure 1:
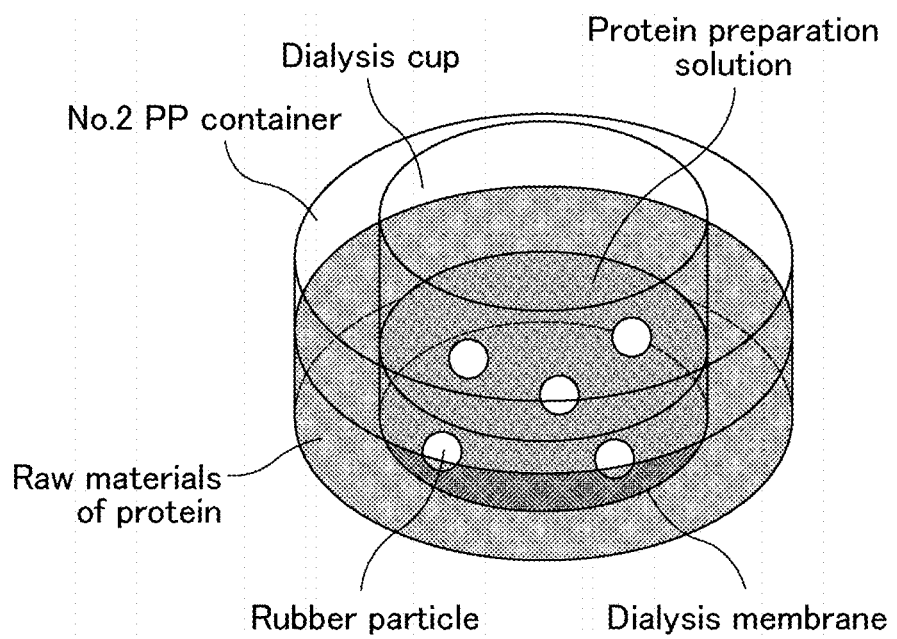
FIG. 1 is an outline diagram illustrating the dialysis process in EXAMPLES.

Herein, the first disclosure and the second disclosure are also referred to collectively as the present disclosure. The first disclosure will be first explained and later the second disclosure will be explained.
(First Disclosure)

The method for producing a polyisoprenoid of the first disclosure includes binding a protein expressed from a gene coding for a neryl diphosphate synthase to rubber particles in vitro.

The inventors were the first to discover that by binding a neryl diphosphate synthase to rubber particles in vitro, it is possible to synthesize polyisoprenoids including a 100% cis-polyisoprenoid in the rubber particles. The neryl diphosphate synthase is presumed to be involved in rubber synthesis with rubber particles by being placed on the rubber particles and then synthesizing neryl diphosphate using isopentenyl diphosphate and dimethylallyl diphosphate as substrates to prepare an initiating terminal (@-terminal) for polyisoprenoid synthesis. More specifically, it is considered that a polyisoprenoid will be be synthesized using as an initiating terminal neryl diphosphate having isoprene units linked in a cis configuration synthesized by the neryl diphosphate synthase, and with the aid of a cis-prenyltransferase or other enzyme which is present on the rubber particles and catalyzes the reaction of cis-chain elongation of an isoprenoid compound, and therefore polyisoprenoids including a 100% cis-polyisoprenoid can be synthesized. Thus, by binding of a neryl diphosphate synthase to rubber particles in vitro, for example in a reaction vessel (e.g., a test tube or industrial plant) as in the production method of the first disclosure, it is possible to synthesize polyisoprenoids including a 100% cis-polyisoprenoid in the rubber particles, and therefore it is possible to efficiently produce polyisoprenoids in a reaction vessel (e.g., a test tube or industrial plant).

Further, wild-type neryl diphosphate synthase allows for elongation of an isoprenoid chain only having up to 10 carbon atoms, and can at most provide only an initiating terminal for polyisoprenoid synthesis. However, the inventors also first discovered that by replacing the helix 3 region, which is considered to contribute to determining the chain length of a product produced by neryl diphosphate synthase, by the helix 3 region of a cis-prenyltransferase capable of producing a medium or longer chain (C35 or greater) isoprenoid chain, the neryl diphosphate synthase itself can synthesize a 100% cis-polyisoprenoid.

It was also discovered that the neryl diphosphate synthase in which the helix 3 region has been replaced has a broad substrate specificity and can synthesize even a polyisoprenoid containing an allyl diphosphate derivative other than the original initiating terminal DNAPP as an initiating terminal.

As the initiating terminal of naturally occurring natural rubber is necessarily a trans-isoprenoid chain, cis-prenyltransferases (CPT) bound to rubber particles had been considered to recognize a trans-isoprenoid chain as an initiating terminal. Since enzymes have a strict substrate specificity, whether cis-neryl diphosphate can be used as an initiating terminal had not been known.

Moreover, as described above, it had been known that neryl diphosphate synthase allows for elongation of an isoprenoid chain only having up to 10 carbon atoms and can synthesize only a short isoprenoid chain.

In this context, according to the production method of the first disclosure, it has become possible to synthesize polyisoprenoids including a 100% cis-polyisoprenoid by binding a neryl diphosphate synthase to rubber particles to allow CPT bound to the rubber particles to utilize a product produced by the neryl diphosphate synthase. This is considered a surprising result which could not have been predicted by skilled persons. Furthermore, by introducing a mutation as described above into a neryl diphosphate synthase and binding it to rubber particles, it has become possible to allow the neryl diphosphate synthase itself to synthesize polyisoprenoids including a polyisoprenoid having an unprecedented structure, e.g., polyisoprenoids including a 100% cis-polyisoprenoid or polyisoprenoids including a polyisoprenoid containing an allylic diphosphate derivative as an initiating terminal. This is also considered a surprising result which could not have been predicted by skilled persons.

Here, the production method of the first disclosure may include any other step as long as it involves the above binding step, and each step may be performed once or repeated multiple times.

Moreover, the amount of the neryl diphosphate synthase to be bound to the rubber particles is not limited in the first disclosure.

Herein, the expression "binding a neryl diphosphate synthase to rubber particles" means, for example, that the neryl diphosphate synthase is fully or partially incorporated into the rubber particles or inserted into the membrane structure of the rubber particles although it is not limited to these embodiments and also includes embodiments in which, for example, the synthase is localized on the surface or inside of the rubber particles. Moreover, the concept of binding to rubber particles also includes embodiments in which the neryl diphosphate synthase forms a complex with a protein bound to the rubber particles to be present in the form of the complex on the rubber particles.

The origin of the rubber particles is not limited. For example, the rubber particles may be derived from the latex of a rubber-producing plant such as Hevea *brasiliensis, Taraxacum kok-saghyz, Parthenium argentatum*, or Sonchus *oleraceus*.

The particle size of the rubber particles is also not limited. Rubber particles having a predetermined particle size may be sorted out and used, or a mixture of rubber particles having different particle sizes may be used. When rubber particles having a predetermined particle size are sorted out and used, the rubber particles used may be either small rubber particles (SRP) having a small particle size or large rubber particles (LRP) having a large particle size.

Commonly used methods may be employed for sorting out the rubber particles having a predetermined particle size, including, for example, methods which involve centrifugation, preferably multistage centrifugation. A specific method includes centrifugation at 500-1500×g, centrifugation at 1700-2500×g, centrifugation at 7000-9000×g, centrifugation at 15000-25000×g, and centrifugation at 40000-60000×g, carried out in that order. Here, the duration of each centrifugation treatment is preferably at least 20 minutes, more preferably at least 30 minutes, still more preferably at least 40 minutes, but is preferably 120 minutes or less, more preferably 90 minutes or less. Moreover, the temperature for each centrifugation treatment is preferably 0 to 10° C., more preferably 2 to 8° C., particularly preferably 4° C.

In the binding step, a protein expressed from a gene coding for a neryl diphosphate synthase is bound to rubber particles in vitro.

The origin of the gene coding for a neryl diphosphate synthase is not limited, and the gene may be derived from a microorganism, an animal, or a plant, preferably a plant, more preferably the genus *Solanum*. In particular, it is particularly preferably derived from tomato.

Herein, the term "neryl diphosphate synthase" refers to an enzyme that catalyzes a reaction to synthesize neryl diphosphate using isopentenyl diphosphate and dimethylallyl diphosphate as substrates. The neryl diphosphate synthase may be, for example, NDPS from tomato.

Herein, the term "isoprenoid compound" refers to a compound having an isoprene unit ($C_5H_8$). Also, the term "cis-isoprenoid" refers to a compound including an isoprenoid compound in which isoprene units are linked in a cis configuration, and examples include neryl diphosphate, cis-farnesyl diphosphate (Z, Z-farnesyl diphosphate), nerylneryl diphosphate, and cis-polyisoprenoids.

Moreover, according to the first disclosure, by binding a neryl diphosphate synthase to rubber particles in vitro, it is possible to synthesize a polyisoprenoid in the rubber particles. As described above, the neryl diphosphate synthase is an enzyme that catalyzes a reaction to synthesize neryl diphosphate in which isoprene units are linked in a cis configuration using isopentenyl diphosphate and dimethylallyl diphosphate as substrates, and it is presumed that the thus synthesized neryl diphosphate may be used as an initiating terminal to allow a reaction of cis-chain elongation of an isoprenoid compound to proceed on the rubber particles to synthesize a polyisoprenoid. Due to the reaction specificity of the enzymes involved in the reaction, it is also presumed that a 100% cis-polyisoprenoid may be synthesized. Thus, it can be regarded that, according to the first disclosure, a 100% cis-polyisoprenoid may be produced in which no trans configuration is present and all isoprene units are linked in a cis configuration. In other words, in another suitable embodiment of the present disclosure, the polyisoprenoid produced according to the first disclosure is a 100% cis-polyisoprenoid.

Also, as described above, according to the first disclosure, it is possible to produce a non-short chain polyisoprenoid in which no trans configuration is present and all isoprene units are linked in a cis configuration. The weight average molecular weight (Mw) of the polyisoprenoid produced according to the first disclosure is preferably 100,000 or greater, more preferably 200,000 or greater, still more preferably 300,000 or greater, particularly preferably 400,000 or greater, most preferably 500,000 or greater, even most preferably 600,000 or greater, further most preferably 700,000 or greater, particularly most preferably 800,000 or greater. Moreover, the upper limit is not limited, but is usually about 2,000,000.

Herein, the weight average molecular weight (Mw) can be determined by gel permeation chromatography (GPC) (GPC-8000 series available from Tosoh Corporation, detector: differential refractometer, column: TSKgel SuperMultipore HZ-M available from Tosoh Corporation) calibrated with polystyrene standards.

The gene coding for a neryl diphosphate synthase is derived from a plant that does not produce rubber, and of course, the neryl diphosphate synthase is not involved in rubber synthesis in nature. In spite of this, according to the present disclosure, any neryl diphosphate synthase may be used to synthesize polyisoprenoids including a 100% cis-polyisoprenoid in rubber particles by being bound to the rubber particles.

The neryl diphosphate synthase used in the present disclosure desirably has a transmembrane domain on the N-terminal side to increase the affinity for rubber particles. In the case of a wild type having no transmembrane domain, a transmembrane domain may be artificially fused to the N-terminal side of the neryl diphosphate synthase. The transmembrane domain to be fused may have any amino acid sequence, desirably an amino acid sequence of the transmembrane domain of a protein inherently bound to rubber particles in nature.

Alternatively, in order to increase the affinity for rubber particles, when the neryl diphosphate synthase used in the present disclosure is a wild type having a signal sequence at the terminal, the signal sequence is preferably removed from the neryl diphosphate synthase before use although the neryl diphosphate synthase may be one with the signal sequence.

The term "signal sequence" refers to a sequence that is present in a protein biosynthesized in a ribosome and can be used for transportation and localization of the protein to each organelle or other location in vivo, and differs for each organelle to which the protein is transported and localized.

For example, in the case of the NDPS from tomato represented by SEQ ID NO: 2, the amino acid sequence at positions 2 to 44 in SEQ ID NO: 2 corresponds to a signal sequence.

The neryl diphosphate synthase is preferably one from which a signal sequence has been removed. A specific example of such a neryl diphosphate synthase is the following protein [1]: [1] a protein having the amino acid sequence represented by SEQ ID NO: 8.

Moreover, it is known that proteins having one or more amino acid substitutions, deletions, insertions, or additions relative to the original amino acid sequence can have the inherent function. Thus, another specific example of the neryl diphosphate synthase is the following protein [2]: [2] a protein having an amino acid sequence containing one or more amino acid substitutions, deletions, insertions, and/or additions relative to the amino acid sequence represented by SEQ ID NO: 8, and having an enzyme activity that catalyzes a reaction to synthesize neryl diphosphate using isopentenyl diphosphate and dimethylallyl diphosphate as substrates.

Here, in order to maintain the function of the neryl diphosphate synthase, it preferably has an amino acid sequence containing one or more, more preferably 1 to 52, still more preferably 1 to 39, further more preferably 1 to 26, still further preferably 1 to 18, particularly preferably 1 to 13, most preferably 1 to 6, even most preferably 1 to 3 amino acid substitutions, deletions, insertions, and/or additions relative to the amino acid sequence represented by SEQ ID NO: 8.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the neryl diphosphate synthase is the following protein [3]:

[3] a protein having an amino acid sequence with at least 80% sequence identity to the amino acid sequence represented by SEQ ID NO: 8, and having an enzyme activity that catalyzes a reaction to synthesize neryl diphosphate using isopentenyl diphosphate and dimethylallyl diphosphate as substrates.

Here, in order to maintain the function of the neryl diphosphate synthase, the sequence identity to the amino acid sequence represented by SEQ ID NO: 8 is preferably at least 85%, more preferably at least 90%, still more preferably at least 93%, further more preferably at least 95%, particularly preferably at least 98%, most preferably at least 99%.

Herein, the sequence identity between amino acid sequences or between nucleotide sequences may be determined using the algorithm BLAST [Pro. Natl. Acad. Sci. USA, 90, 5873 (1993)] developed by Karlin and Altschul or FASTA [Methods Enzymol., 183, 63 (1990)].

Whether it is a protein having the above enzyme activity may be determined by, for example, conventional techniques, such as by expressing a target protein in a transformant produced by introducing a gene coding for the target protein into *Escherichia coli* or other host organism, and determining the presence or absence of the function of the target protein by the corresponding activity measuring method.

The gene coding for a neryl diphosphate synthase is not limited as long as it codes for the neryl diphosphate synthase to express and produce the neryl diphosphate synthase. As described above, the neryl diphosphate synthase is preferably one from which a signal sequence has been removed. Specific examples of such genes coding for a neryl diphosphate synthase include the following DNAs [1] and [2]:

[1] a DNA having the nucleotide sequence represented by SEQ ID NO: 7; and

[2] a DNA which hybridizes under stringent conditions to a DNA having a nucleotide sequence complementary to the nucleotide sequence represented by SEQ ID NO: 7, and which codes for a protein having an enzyme activity that catalyzes a reaction to synthesize neryl diphosphate using isopentenyl diphosphate and dimethylallyl diphosphate as substrates.

Here, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases, but it may be a DNA of at least 10 bases, preferably at least 15 bases.

Techniques to perform DNA hybridization experiments are well known. The hybridization conditions under which experiments are carried out may be determined according to, for example, Molecular Cloning, 2nd ed. and 3rd ed. (2001), Methods for General and Molecular Bacteriology, ASM Press (1994), Immunology methods manual, Academic press (Molecular), or many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/L denatured salmon sperm DNA, followed by washing the filter for example in a 0.2×SSC solution at approximately 65° C. Less stringent conditions may also be used. Changes in stringency may be accomplished through the manipulation of the formamide concentration (lower percentages of formamide result in lower stringency), salt concentrations, or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, PH 7.4), 0.5% SDS, 30% formamide, and 100 µg/L denatured salmon sperm DNA, followed by washing in a 1×SSC solution containing 0.1% SDS at 50° C. In addition, to achieve even lower stringency, washes performed following hybridization may be done at higher salt concentrations (e.g., 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO: 7 as calculated using a program such as BLAST or FASTA with the parameters mentioned above.

Whether the DNA which hybridizes to the above-mentioned DNA under stringent conditions is a DNA coding for a protein having a predetermined enzyme activity may be determined by conventional techniques, such as by expressing a target protein in a transformant produced by introducing a gene coding for the target protein into *Escherichia coli* or other host organism, and determining the presence or absence of the function of the target protein by the corresponding activity measuring method.

Moreover, conventional techniques may be employed to identify the amino acid sequence or nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence or amino acid sequence is identified, e.g. by the RACE method. The RACE method (rapid amplification of cDNA ends method) refers to a method in which, when the nucleotide sequence of a cDNA is partially known, PCR is performed based on the nucleotide sequence data of such a known region to clone the unknown region extending to the cDNA terminal. This method can clone full-length cDNA by PCR without preparing a cDNA library.

Here, the degenerate primers may each preferably be prepared from a plant-derived sequence having a highly similar sequence part to the target protein.

Moreover, if the nucleotide sequence coding for the protein is known, the full-length nucleotide sequence or amino acid sequence can be identified by designing a primer containing a start codon and a primer containing a stop codon using the known nucleotide sequence, followed by performing RT-PCR using a synthesized cDNA as a template.

The neryl diphosphate synthase is preferably a mutant protein obtained by replacing the helix 3 region by the helix 3 region of a cis-prenyltransferase capable of producing an isoprenoid chain having 35 or greater carbon atoms.

The helix 3 region of a neryl diphosphate synthase is considered to contribute to determining the chain length of a product produced by the neryl diphosphate synthase. For example, in the case of the amino acid sequence of NDPS from tomato represented by SEQ ID NO: 2, the helix 3 region corresponds to the amino acid sequence at positions 147 to 163.

When the neryl diphosphate synthase is a mutant protein as described above, as the helix 3 region, which is considered to contribute to determining the chain length of a product produced by neryl diphosphate synthase, is replaced by the sequence of the helix 3 region of a cis-prenyltransferase capable of producing a medium or longer chain (C35 or greater) isoprenoid chain, the neryl diphosphate synthase itself can synthesize a 100% cis-polyisoprenoid. Furthermore, when the neryl diphosphate synthase is a mutant protein as described above, the binding ability to rubber particles can be increased owing to the effect of the helix 3 region.

When the helix 3 region of a neryl diphosphate synthase and the helix 3 region of a cis-prenyltransferase capable of producing an isoprenoid chain having 35 or greater carbon atoms by which the helix 3 region of a neryl diphosphate synthase is to be replaced are each compared by amino acid multiple alignment with undecaprenyl diphosphate synthase (UPS) from *Micrococcus* (*Micrococcus luteus* B-P 26) whose crystal structure is known, each helix 3 region can be defined as a region corresponding to the helix 3 region of the UPS from *Micrococcus* (the amino acid sequence at positions 90 to 110 (KLPGDFLNTFLPELIEKNVKV) of undecaprenyl diphosphate synthase (UPS) from *Micrococcus* (*Micrococcus luteus* B-P 26) represented by SEQ ID NO: 15). Thus, based on this definition, skilled persons can unambiguously determine the helix 3 region from the amino acid sequence of a neryl diphosphate synthase or the amino acid sequence of a cis-prenyltransferase capable of producing an isoprenoid chain having 35 or greater carbon atoms.

The helix 3 region of a neryl diphosphate synthase is preferably replaced by the amino acid sequence of the helix 3 region of a cis-prenyltransferase capable of producing an isoprenoid chain having 35 or greater carbon atoms or an amino acid sequence having at least 80% sequence identity to the amino acid sequence. The sequence identity is more preferably at least 85%, still more preferably at least 90%, particularly preferably at least 95%, most preferably at least 98%, even most preferably at least 99%.

Here, examples of the cis-prenyltransferase (CPT) capable of producing an isoprenoid chain having 35 or greater carbon atoms include CPT from *Hevea brasiliensis* (HRT1, HRT2, CPT3 to CPT5), CPT from *Arabidopsis thaliana* (AtCPT1 to AtCPT9), CPT1 to CPT3 from *Lactuca sativa*, CPT1 to CPT3 from *Taraxacum brevicorniculatum*, CPT from *Taraxacum kok-saghyz*, undecaprenyl pyrophosphate synthase (UPPS) from *Escherichia coli*, undecaprenyl diphosphate synthase (UPS) from *Micrococcus*, SRT1 from yeast, DDPS from tobacco, DDPS from mouse, and HDS from human. Among these, CPT from *Hevea brasiliensis*, CPT from *Arabidopsis thaliana*, and CPT from *Taraxacum kok-saghyz* are preferred, CPT from *Hevea brasiliensis* and CPT from *Arabidopsis thaliana* are more preferred, and CPT from *Hevea brasiliensis* is still more preferred.

More specifically, in a suitable embodiment of the present disclosure, the helix 3 region of a neryl diphosphate synthase is replaced by the amino acid sequence of the helix 3 region at positions 147 to 167 (SLFERSLKTEFONLAKNNVRI) of CPT4 from *Arabidopsis thaliana* (AtCPT4) represented by SEQ ID NO: 13.

Other specific examples of the helix 3 region of a cis-prenyltransferase (CPT) capable of producing an isoprenoid chain having 35 or greater carbon atoms include the amino acid sequence at positions 86 to 106 (ELFVWALDSEVKSLHRHNVRL) of undecaprenyl pyrophosphate synthase (UPPS) from *Escherichia coli* represented by SEQ ID NO: 14, the amino acid sequence at positions 136 to 161 (NLFTVKLDEFAKRAKDYKDPLYGSKI) of SRT1 from yeast represented by SEQ ID NO: 16, and the amino acid sequence at positions 95 to 118 (DLARQKFSRLMEEKEKLOKHGVCI) of HDS from human represented by SEQ ID NO: 17.

Here, FIG. 5 shows an outline diagram illustrating the results of multiple sequence alignment of cis-prenyltransferases derived from various organisms, each capable of producing an isoprenoid chain having 35 or greater carbon atoms. Based on the results, skilled persons can understand that the helix 3 region of undecaprenyl diphosphate synthase (UPS) from *Micrococcus* (*Micrococcus luteus* B-P 26) (the amino acid sequence at positions 90 to 110 of undecaprenyl diphosphate synthase (UPS) from *Micrococcus* (*Micrococcus luteus* B-P 26) represented by SEQ ID NO: 15) corresponds to the amino acid sequence at positions 86 to 106 of undecaprenyl pyrophosphate synthase (UPPS) from *Escherichia coli* represented by SEQ ID NO: 14 in the case of undecaprenyl pyrophosphate synthase (UPPS) from *Escherichia coli*, the amino acid sequence at positions 136 to 161 of SRT1 from yeast represented by SEQ ID NO: 16 in the case of SRT1 from yeast, and the amino acid sequence at positions 95 to 118 of HDS from human represented by SEQ ID NO: 17 in the case of HDS from human. In FIG. 5, each helix 3 region is surrounded by the frame. Here, the multiple sequence alignment can be carried out as described later in EXAMPLES.

A specific example of the mutant protein is the following protein [4]:

[4] a protein having the amino acid sequence represented by SEQ ID NO: 12.

Moreover, it is known that proteins having one or more amino acid substitutions, deletions, insertions, or additions relative to the original amino acid sequence can also have similar functions. Thus, another specific example of the mutant protein is the following protein [5]:

[5] a protein having an amino acid sequence containing one or more amino acid substitutions, deletions, insertions, and/or additions relative to the amino acid sequence represented by SEQ ID NO: 12, and having an enzyme activity that catalyzes a reaction to synthesize an a 100% cis-polyisoprenoid using isopentenyl diphosphate and dimethylallyl diphosphate as substrates.

Here, in order to maintain the function described above, the protein preferably has an amino acid sequence containing one or more, more preferably 1 to 53, still more preferably 1 to 40, further preferably 1 to 27, particularly preferably 1 to 14, most preferably 1 to 6, even most preferably 1 to 3 amino acid substitutions, deletions, insertions, and/or additions relative to the amino acid sequence represented by SEQ ID NO: 12.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the mutant protein is the following protein [6]: [6] a protein having an amino acid sequence with at least 80% sequence identity to the amino acid sequence represented by SEQ ID NO: 12, and having an enzyme activity that catalyzes a reaction to synthesize a 100% cis-polyisoprenoid using isopentenyl diphosphate and dimethylallyl diphosphate as substrates.

Here, in order to maintain the function described above, the sequence identity to the amino acid sequence represented by SEQ ID NO: 12 is preferably at least 858, more preferably at least 90%, still more preferably at least 95%, particularly preferably at least 98%, most preferably at least 99%.

Whether it is a protein having the above enzyme activity may be determined as described above.

Specific examples of the gene coding for the mutant protein include the following DNAs [3] and [4]:
 [3] a DNA having the nucleotide sequence represented by SEQ ID NO: 11; and
 [4] a DNA which hybridizes under stringent conditions to a DNA having a nucleotide sequence complementary to the nucleotide sequence represented by SEQ ID NO: 11, and which codes for a protein having an enzyme activity that catalyzes a reaction to synthesize a 100% cis-polyisoprenoid using isopentenyl diphosphate and dimethylallyl diphosphate as substrates.

Here, the term "hybridize" is as described above. Also, the term "stringent conditions" is as described above.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO: 11 as calculated using a program such as BLAST or FASTA with the parameters mentioned above.

Whether the DNA which hybridizes to the above-mentioned DNA under stringent conditions is a DNA coding for a protein having a predetermined enzyme activity may be determined as described above.

Here, the amino acid sequence or nucleotide sequence of the protein may be identified as described above.

Furthermore, when the origin of the cis-prenyltransferase (CPT) capable of producing an isoprenoid chain having 35 or greater carbon atoms is the same as the origin of an enzyme bound to the rubber particles to be bound to the neryl diphosphate synthase, the origin of the helix 3 region of the cis-prenyltransferase capable of producing an isoprenoid chain having 35 or greater carbon atoms by which the helix 3 region of the neryl diphosphate synthase is to be replaced is the same as the origin of the rubber particles to be bound to the neryl diphosphate synthase, and the binding ability between the neryl diphosphate synthase and rubber particles can be further increased as CPT and rubber particles of the same origin are bound to each other in nature.

For example, when rubber particles derived from Hevea *brasiliensis* are used, it is preferred to use a mutant protein obtained by replacing the helix 3 region of a neryl diphosphate synthase by the helix 3 region of CPT from Hevea *brasiliensis* (HRT1, HRT2, CPT3). Alternatively, when rubber particles derived from *Taraxacum kok-saghyz* are used, it is preferred to use a mutant protein obtained by replacing the helix 3 region of a neryl diphosphate synthase by the helix 3 region of CPT from *Taraxacum kok-saghyz*.

More specifically, in another suitable embodiment of the present disclosure, when rubber particles derived from Hevea *brasiliensis* are used, the helix 3 region of a neryl diphosphate synthase is replaced by the amino acid sequence of the helix 3 region at positions 102 to 125 (DLMLEKIEG-MIMEESIINAYDICV) of CPT from Hevea *brasiliensis* (HRT1) represented by SEQ ID NO: 24.

In this case, a specific example of the mutant protein is the following protein [7]:
 [7] a protein having the amino acid sequence represented by SEQ ID NO: 19.

Moreover, it is known that proteins having one or more amino acid substitutions, deletions, insertions, or additions relative to the original amino acid sequence can have similar functions. Thus, another specific example of the mutant protein is the following protein [8]:
 [8] a protein having an amino acid sequence containing one or more amino acid substitutions, deletions, insertions, and/or additions relative to the amino acid sequence represented by SEQ ID NO: 19, and having an enzyme activity that catalyzes a reaction to synthesize a 100% cis-polyisoprenoid using isopentenyl diphosphate and dimethylallyl diphosphate as substrates.

Here, in order to maintain the function described above, the protein preferably has an amino acid sequence containing one or more, more preferably 1 to 53, still more preferably 1 to 40, further preferably 1 to 27, particularly preferably 1 to 14, most preferably 1 to 6, even most preferably 1 to 3 amino acid substitutions, deletions, insertions, and/or additions relative to the amino acid sequence represented by SEQ ID NO: 19.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the mutant protein is the following protein [9]: [9] a protein having an amino acid sequence with at least 80% sequence identity to the amino acid sequence represented by SEQ ID NO: 19, and having an enzyme activity that catalyzes a reaction to synthesize a 100% cis-polyisoprenoid using isopentenyl diphosphate and dimethylallyl diphosphate as substrates.

Here, in order to maintain the function described above, the sequence identity to the amino acid sequence represented by SEQ ID NO: 19 is preferably at least 85%, more preferably at least 90%, still more preferably at least 95%, particularly preferably at least 98%, most preferably at least 99%.

Whether it is a protein having the above enzyme activity may be determined as described above.

Specific examples of the gene coding for the mutant protein include the following DNAs [5] and [6]: [5] a DNA having the nucleotide sequence represented by SEQ ID NO: 18; and

[6] a DNA which hybridizes under stringent conditions to a DNA having a nucleotide sequence complementary to the nucleotide sequence represented by SEQ ID NO: 18, and which codes for a protein having an enzyme activity that catalyzes a reaction to synthesize a 100% cis-polyisoprenoid using isopentenyl diphosphate and dimethylallyl diphosphate as substrates.

Here, the term "hybridize" is as described above. Also, the term "stringent conditions" is as described above.

The DNA capable of hybridizing under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO: 18 as calculated using a program such as BLAST or FASTA with the parameters mentioned above.

Whether the DNA which hybridizes to the above-mentioned DNA under stringent conditions is a DNA coding for a protein having a predetermined enzyme activity may be determined as described above.

Here, the amino acid sequence or nucleotide sequence of the protein may be identified as described above.

Here, in the binding step, an additional protein may further be bound to the rubber particles as long as the protein expressed from a gene coding for a neryl diphosphate synthase is bound to the rubber particles in vitro.

The origin of the additional protein is not limited, but the additional protein is preferably derived from a plant, more preferably a rubber-producing plant, still more preferably at least one selected from the group consisting of plants of the genera Hevea, Sonchus, Taraxacum, and Parthenium. In particular, it is further more preferably derived from at least one species of plant selected from the group consisting of Hevea brasiliensis, Sonchus oleraceus, Parthenium argentatum, and Taraxacum kok-saghyz, particularly preferably from Hevea brasiliensis.

The additional protein may be any protein without any limitations, but from the standpoint of the rubber synthesis ability of the rubber particles, it is preferably a protein that is inherently present on rubber particles in a rubber-producing plant. Here, the protein present on rubber particles may be a protein that binds to a large part of the membrane surface of rubber particles, or a protein that binds to the membrane of rubber particles so as to be inserted thereinto, or a protein that forms a complex with another protein bound to the membrane to be present on the membrane surface.

Examples of the protein that is inherently present on rubber particles in a rubber-producing plant include cis-prenyltransferase (CPT), Nogo-B receptor (NgBR), rubber elongation factor (REF), small rubber particle protein (SRPP), β-1,3-glucanase, and Hevein.

The binding step may be carried out using any means that can bind a neryl diphosphate synthase to rubber particles in vitro, such as, for example, by performing protein synthesis in the presence of both rubber particles and a cell-free protein synthesis solution containing an mRNA coding for a neryl diphosphate synthase to bind the neryl diphosphate synthase to the rubber particles.

The binding step preferably includes performing protein synthesis in the presence of both rubber particles and a cell-free protein synthesis solution containing an mRNA coding for a neryl diphosphate synthase to bind the neryl diphosphate synthase to the rubber particles, among other methods.

In other words, it is preferred to obtain rubber particles bound to a neryl diphosphate synthase by performing protein synthesis in the presence of both rubber particles and a cell-free protein synthesis solution containing an mRNA coding for the neryl diphosphate synthase, or, more specifically, using a mixture of rubber particles with a cell-free protein synthesis solution containing an mRNA coding for the neryl diphosphate synthase.

Here, since liposomes are artificially produced as lipid bilayer membranes consisting of phospholipids, glyceroglycolipids, cholesterol, and other components, no protein is bound to the surface of the produced liposomes. In contrast, although rubber particles collected from the latex of rubber-producing plants are also coated with a lipid membrane, the membrane of the rubber particles is a naturally derived membrane in which proteins that have been synthesized in the plant are already bound to the surface of the membrane. In view of this, it is expected to be more difficult to bind an additional protein to rubber particles that are already bound to and coated with proteins than to bind it to liposomes not bound to any protein. There is also concern that the proteins already bound to rubber particles could inhibit cell-free protein synthesis. For these reasons, difficulties have been anticipated in achieving cell-free protein synthesis in the presence of rubber particles. Under such circumstances, the present inventors conducted cell-free synthesis of a neryl diphosphate synthase in the presence of rubber particles, which had never been attempted in the past, and it was then found that it is possible to produce rubber particles bound to a neryl diphosphate synthase.

The protein synthesis performed in the presence of both rubber particles and a cell-free protein synthesis solution containing an mRNA coding for a neryl diphosphate synthase is namely the synthesis of a neryl diphosphate synthase by cell-free protein synthesis, and the synthesized neryl diphosphate synthase maintains its biological function (native state). As the cell-free protein synthesis is performed in the presence of rubber particles, the synthesized neryl diphosphate synthase in the native state can be bound to the rubber particles.

Here, "performing protein synthesis in the presence of both the cell-free protein synthesis solution and rubber particles to bind the neryl diphosphate synthase to the rubber particles" means, for example, that each neryl diphosphate synthase protein synthesized by the protein synthesis is fully or partially incorporated into the rubber particles or inserted into the membrane structure of the rubber particles. It is not limited to these embodiments and also means embodiments in which the protein is localized on the surface or inside of the rubber particles. Moreover, the concept of binding to rubber particles also includes embodiments in which the protein forms a complex with another protein bound to the rubber particles as described above to be present in the form of the complex on the rubber particles.

Each mRNA coding for a neryl diphosphate synthase serves as a translation template that can be translated to synthesize the neryl diphosphate synthase.

The origin of the mRNA coding for a neryl diphosphate synthase is not limited, and the mRNA may be derived from a microorganism, an animal, or a plant, preferably a plant, more preferably the genus *Solanum*. In particular, it is particularly preferably derived from tomato.

Each mRNA coding for a neryl diphosphate synthase may be prepared by any method as long as the prepared mRNA serves as a translation template that can be translated to synthesize the neryl diphosphate synthase. For example, the mRNA may be prepared by extracting total RNA from leaves of a plant by, for example, the hot phenol method, synthesizing cDNA from the total RNA, obtaining a DNA fragment of a gene coding for a neryl diphosphate synthase using primers prepared based on the nucleotide sequence data of the gene coding for a neryl diphosphate synthase, and performing an ordinary in vitro transcription reaction of the DNA fragment.

As long as the cell-free protein synthesis solution contains the mRNA coding for a neryl diphosphate synthase, it may contain an mRNA coding for an additional protein.

The mRNA coding for an additional protein may be one that can be translated to express the additional protein. Here, the additional protein may be as described above.

In the binding step in the first disclosure, cell-free protein synthesis of a neryl diphosphate synthase is preferably performed in the presence of rubber particles. This cell-free protein synthesis may be carried out using the cell-free protein synthesis solution in a similar manner to conventional methods. The cell-free protein synthesis system used may be a common cell-free protein synthesis means, such as rapid translation system RTS500 (Roche Diagnostics); or wheat germ extracts prepared in accordance with Proc. Natl. Acad. Sci. USA, 97:559-564 (2000), JP 2000-236896 A, JP 2002-125693 A, and JP 2002-204689 A, or their cell-free protein synthesis systems (JP 2002-204689 A, Proc. Natl. Acad. Sci. USA, 99:14652-14657 (2002)). Systems using germ extracts are preferred among these. Thus, in another suitable embodiment of the first disclosure, the cell-free protein synthesis solution contains a germ extract.

The source of the germ extract is not limited. From the standpoint of translation efficiency, it is preferred to use a plant-derived germ extract for cell-free protein synthesis of a plant protein. It is particularly preferred to use a wheat-derived germ extract. Thus, in another suitable embodiment of the first disclosure, the germ extract is derived from wheat.

The method for preparing the germ extract is not limited, and may be carried out conventionally, as described in, for example, JP 2005-218357 A.

The cell-free protein synthesis solution preferably further contains a cyclic nucleoside monophosphate derivative or a salt thereof (hereinafter, also referred to simply as "activity enhancer"). Protein synthesis activity can be further enhanced by the inclusion of the activity enhancer.

The cyclic nucleoside monophosphate derivative or salt thereof is not limited as long as it can enhance cell-free protein synthesis activity. Examples include adenosine-3', 5'-cyclic monophosphoric acid and its salts; adenosine-3', 5'-cyclic monophosphorothioic acid (Sp-isomer) and its salts; adenosine-3', 5'-cyclic monophosphorothioic acid (Rp-isomer) and its salts; guanosine-3', 5'-cyclic monophosphoric acid and its salts; guanosine-3', 5'-cyclic monophosphorothioic acid (Sp-isomer) and its salts; guanosine-3', 5'-cyclic monophosphorothioic acid (Rp-isomer) and its salts; 8-bromoadenosine-3', 5'-cyclic monophosphoric acid (bromo-CAMP) and its salts; 8-(4-chlorophenylthio) adenosine-3', 5'-cyclic monophosphoric acid (chlorophenyl-thio-CAMP) and its salts; 5,6-dichloro-1-3-D-ribofuranosyl-benzimidazole adenosine-3', 5'-cyclic monophosphoric acid (dichlororibofuranosylbenzimidazole CAMP) and its salts; adenosine-2', 5'-cyclic monophosphoric acid and its salts; adenosine-2', 5'-cyclic monophosphorothioic acid (Sp-isomer) and its salts; adenosine-2', 5'-cyclic monophosphorothioic acid (Rp-isomer) and its salts; guanosine-2', 5'-cyclic monophosphoric acid and its salts; guanosine-2', 5'-cyclic monophosphorothioic acid (Sp-isomer) and its salts; and guanosine-2', 5'-cyclic monophosphorothioic acid (Rp-isomer) and its salts.

The base that can form a salt with the cyclic nucleoside monophosphate derivative is not limited as long as it is biochemically acceptable and can form a salt with the derivative. Preferred are, for example, alkali metal atoms such as sodium or potassium, and organic bases such as tris-hydroxyaminomethane, among others.

Among these activity enhancers, adenosine-3', 5'-cyclic monophosphoric acid or adenosine-3', 5'-cyclic monophosphate sodium salt is particularly preferred. Moreover, these activity enhancers may be used alone or in combinations of two or more.

The activity enhancer may be added to the cell-free protein synthesis solution in advance, but if the activity enhancer is unstable in the solution, it is preferably added during the protein synthesis reaction performed in the presence of both the cell-free protein synthesis solution and rubber particles.

The amount of the activity enhancer(s) added is not limited as long as it is at a concentration that can activate (increase) the protein synthesis reaction in the cell-free protein synthesis solution. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

The temperature of the cell-free protein synthesis solution to which the activity enhancer is added is not limited, but is preferably 0 to 30° C., more preferably 10 to 26° C.

In addition to the mRNA (translation template) coding for a neryl diphosphate synthase, the cell-free protein synthesis solution also contains ATP, GTP, creatine phosphate, creatine kinase, L-amino acids, potassium ions, magnesium ions, and other components required for protein synthesis, and optionally an activity enhancer. Such a cell-free protein synthesis solution can serve as a cell-free protein synthesis reaction system.

Here, since the germ extract prepared as described in JP 2005-218357 A contains tRNA in an amount necessary for protein synthesis reaction, addition of separately prepared tRNA is not required when the germ extract prepared as above is used in the cell-free protein synthesis solution. In other words, tRNA may be added to the cell-free protein synthesis solution, if necessary.

The binding step in the first disclosure preferably includes performing protein synthesis in the presence of both rubber particles and a cell-free protein synthesis solution containing an mRNA coding for a neryl diphosphate synthase. Specifically, this can be accomplished by adding rubber particles to the cell-free protein synthesis solution at a suitable point either before or after the protein synthesis, preferably before the protein synthesis.

Moreover, the rubber particles are preferably present at a concentration of 5 to 50 g/L in the cell-free protein synthesis solution. In other words, 5 to 50 g of rubber particles are preferably present in 1 L of the cell-free protein synthesis solution. If the concentration of rubber particles present in the cell-free protein synthesis solution is less than 5 g/L, a rubber layer may not be formed by separation treatment (e.g., ultracentrifugation) for collecting the rubber particles bound to the synthesized neryl diphosphate synthase, and therefore it may be difficult to collect the rubber particles bound to the synthesized neryl diphosphate synthase. Moreover, if the concentration of rubber particles present in the cell-free protein synthesis solution exceeds 50 g/L, the rubber particles may aggregate, so that the synthesized neryl diphosphate synthase may fail to bind well to the rubber particles. The concentration of rubber particles is more preferably 10 to 40 g/L, still more preferably 15 to 35 g/L, particularly preferably 15 to 30 g/L.

Moreover, in the protein synthesis in the presence of both rubber particles and the cell-free protein synthesis solution, additional rubber particles may be appropriately added as the reaction progresses. The cell-free protein synthesis solution and rubber particles are preferably present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g., pretreatment, before use in the binding step in the first disclosure, preferably before being combined with the cell-free protein synthesis solution. However, proteins may be removed from the rubber particles with a surfactant beforehand to increase the proportion of the neryl diphosphate synthase desired to be bound by the method of the first disclosure, among the proteins present on the rubber particles. Then, the rubber particles after the removal preferably have a rubber synthesis activity that is at least 50% of that before the removal. Thus, in another suitable embodiment of the first disclosure, the rubber particles used in the first disclosure are washed with a surfactant before use in the binding step in the first disclosure, more preferably before being combined with the cell-free protein synthesis solution.

The surfactant is not limited, and examples include nonionic surfactants and amphoteric surfactants. Nonionic or amphoteric surfactants, among others, are suitable because they have only a little denaturing effect on the proteins on the membrane, and amphoteric surfactants are especially suitable. Thus, in another suitable embodiment of the first disclosure, the surfactant is an amphoteric surfactant.

These surfactants may be used alone or in combinations of two or more.

Examples of the nonionic surfactants include polyoxyalkylene ether nonionic surfactants, polyoxyalkylene ester nonionic surfactants, polyhydric alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Polyoxyalkylene ether or polyhydric alcohol fatty acid ester nonionic surfactants are preferred among these.

Examples of the polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyrylphenyl ethers. Among these, polyoxyalkylene alkylphenyl ethers are suitable. Here, the "polyol" is preferably a C2-C12 polyhydric alcohol, such as ethylene glycol, propylene glycol, glycerin, sorbitol, glucose, sucrose, pentaerythritol, or sorbitan.

Examples of the polyoxyalkylene ester nonionic surfactants include polyoxyalkylene fatty acid esters and polyoxyalkylene alkyl rosin acid esters.

Examples of the polyhydric alcohol fatty acid ester nonionic surfactants include fatty acid esters of C2-C12 polyhydric alcohols and fatty acid esters of polyoxyalkylene polyhydric alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing such as polyoxyalkylene sorbitan fatty acid esters and polyoxyalkylene glycerin fatty acid esters. Among these, sorbitan fatty acid esters are suitable.

Examples of the sugar fatty acid ester nonionic surfactants include fatty acid esters of sucrose, glucose, maltose, fructose, and polysaccharides, as well as polyalkylene oxide adducts of the foregoing.

Examples of the alkyl polyglycoside nonionic surfactants include those having, for example, glucose, maltose, fructose, or sucrose as the glycoside, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include C4-C30 linear or branched, saturated or unsaturated alkyl groups. Moreover, the polyoxyalkylene groups may have C2-C4 alkylene groups, and may have about 1 to 50 moles of added ethylene oxide, for example. Moreover, examples of the fatty acids include C4-C30 linear or branched, saturated or unsaturated fatty acids.

Among the nonionic surfactants, polyoxyethyleneethylene (10) octylphenyl ether (Triton X-100) or sorbitan monolaurate (Span 20) is particularly preferred for their ability to moderately remove membrane-associated proteins while keeping the membrane of rubber particles stable and, further, having only a little denaturing effect on the proteins.

Examples of the amphoteric surfactants include zwitterionic surfactants such as quaternary ammonium salt group/sulfonate group ($-SO_3H$) surfactants, (water-soluble) quaternary ammonium salt group/phosphate group surfactants, (water-insoluble) quaternary ammonium salt group/phosphate group surfactants, and quaternary ammonium salt group/carboxyl group surfactants. Here, the acid group in each surfactant may be a salt.

In particular, such a zwitterionic surfactant preferably has both positive and negative charges in a molecule. The acid dissociation constant (pKa) of the acid group is preferably 5 or less, more preferably 4 or less, still more preferably 3 or less.

Specific examples of the amphoteric surfactants include ammonium sulfobetaines such as 3-[(3-cholamidopropyl) dimethylamino]-2-hydroxy-1-propanesulfonate (CHAPSO), 3-[(3-cholamidopropyl)-dimethylamino]-propanesulfonate (CHAPS), N, N-bis(3-D-gluconamidopropyl)-cholamide, n-octadecyl-N, N'-dimethyl-3-amino-1-propanesulfonate, n-decyl-N, N'-dimethyl-3-amino-1-propanesulfonate, n-dodecyl-N, N'-dimethyl-3-amino-1-propanesulfonate, n-tetradecyl-N, N'-dimethyl-3-amino-1-propanesulfonate (Zwittergent™-3-14), n-hexadecyl-N, N'-dimethyl-3-amino-1-propanesulfonate, and n-octadecyl-N, N'-dimethyl-3-amino-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Among these, 3-[(3-cholamidopropyl)dimethylamino]-propanesulfonate (CHAPS) is particularly preferred for its ability to moderately remove proteins while keeping the membrane of rubber particles stable.

The surfactant concentration for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. Moreover, the lower limit is preferably at least 0.05 times, more preferably at least 0.1 times, still more preferably at least 0.3 times the CMC.

Examples of reaction systems or apparatuses for protein synthesis that can be used in the cell-free protein synthesis include a batch method (Pratt, J. M. et al., Transcription and Translation, Hames, 179-209, B.D. & Higgins, S., eds, IRL Press, Oxford (1984)), a continuous cell-free protein synthesis system in which amino acids, energy sources, and other components are supplied continuously to the reaction system (Spirin, A. S. et al., Science, 242, 1162-1164 (1988)), a dialysis method (Kigawa et al., 21st Annual Meeting of the Molecular Biology Society of Japan, WID 6), and an overlay method (instruction manual of PROTEIOS™ wheat germ cell-free protein synthesis core kit, Toyobo Co., Ltd.). Other methods may include supplying template RNA, amino acids, energy sources, and other components, if necessary, to the protein synthesis reaction system, and discharging the synthesis product or decomposition product as required.

Among these, the dialysis method is preferred. The reason for this is as follows. The overlay method has the advantage of easy operation, but unfortunately rubber particles disperse in the reaction solution and thus are difficult to efficiently bind to the synthesized neryl diphosphate synthase. In contrast, in the dialysis method, since the amino acids used as raw materials of the neryl diphosphate synthase to be synthesized can pass through the dialysis membrane while rubber particles cannot pass therethrough, it is possible to prevent dispersal of rubber particles and thus to efficiently bind the synthesized neryl diphosphate synthase to rubber particles.

Here, the dialysis method refers to a method in which protein synthesis is performed using an apparatus in which the synthesis reaction solution for protein synthesis used in the cell-free protein synthesis is used as an internal dialysis solution and is separated from an external dialysis solution by a dialysis membrane capable of mass transfer. Specifically, for example, the synthesis reaction solution excluding the translation template is optionally pre-incubated for an appropriate amount of time, to which is then added the translation template and the mixture is put in an appropriate dialysis container as the internal reaction solution. Examples of the dialysis container include containers with a dialysis membrane attached to the bottom (e.g., Dialysis Cup 12,000 available from Daiichi Kagaku) and dialysis tubes (e.g., 12,000 available from Sanko Junyaku Co., Ltd.). The dialysis membrane used may have a molecular weight cutoff of 10,000 daltons or more, preferably about 12,000 daltons.

The external dialysis solution used may be a buffer containing amino acids. Dialysis efficiency can be increased by replacing the external dialysis solution with a fresh one when the reaction speed declines. The reaction temperature and time may be selected appropriately according to the protein synthesis system used. For example, in the case of a system using a wheat-derived germ extract, the reaction may be carried out usually at 10 to 40° C., preferably 18 to 30° C., more preferably 20 to 26° C., for 10 minutes to 48 hours, preferably for 10 minutes to 30 hours, more preferably for 10 minutes to 24 hours.

Moreover, since the mRNA coding for a neryl diphosphate synthase contained in the cell-free protein synthesis solution is easily broken down, the mRNA may be additionally added as appropriate during the protein synthesis reaction to make the protein synthesis more efficient. Thus, in another suitable embodiment of the first disclosure, the mRNA coding for a neryl diphosphate synthase is additionally added during the protein synthesis reaction.

Here, the addition time, the number of additions, the addition amount, and other conditions of the mRNA are not limited, and may be selected appropriately.

In the production method of the first disclosure, the step of binding a protein expressed from a gene coding for a neryl diphosphate synthase to rubber particles in vitro may optionally be followed by collecting the rubber particles.

The rubber particle collection step may be carried out by any method that can collect the rubber particles. It may be carried out by conventional methods for collecting rubber particles. Specific examples include methods using centrifugation. When the rubber particles are collected by the centrifugation methods, the centrifugal force, centrifugation time, and centrifugation temperature may be selected appropriately so as to be able to collect the rubber particles. For example, the centrifugal force during the centrifugation is preferably 15000×g or more, more preferably 20000×g or more, still more preferably 25000×g or more. However, since increasing the centrifugal force too much is not expected to produce a correspondingly high separation effect, the upper limit of the centrifugal force is preferably 50000×g or less, more preferably 45000×g or less. The centrifugation time is preferably at least 20 minutes, more preferably at least 30 minutes, still more preferably at least 40 minutes. However, since increasing the centrifugation time too much is not expected to produce a correspondingly high separation effect, the upper limit of the centrifugation time is preferably 120 minutes or less, more preferably 90 minutes or less.

Moreover, from the standpoint of maintaining the protein activity of the neryl diphosphate synthase bound to rubber particles, the centrifugation temperature is preferably 0 to 10° C., more preferably 2 to 8° C., particularly preferably 4° C.

For example, when the cell-free protein synthesis is performed, the rubber particles and the cell-free protein synthesis solution are separated into the upper and lower layers, respectively, by the centrifugation. The cell-free protein synthesis solution as the lower layer may then be removed to collect the rubber particles bound to the neryl diphosphate synthase. The collected rubber particles may be re-suspended in an appropriate buffer with a neutral pH for storage.

Here, the rubber particles collected by the rubber particle collection step can be used in the same way as usual natural rubber without the need for further special treatment.

Further, the polyisoprenoid produced by the method for producing a polyisoprenoid of the first disclosure can be recovered by subjecting the rubber particles to the solidification step described below.

The solidification step may be carried out by any solidification method, such as by adding the rubber particles to a solvent that does not dissolve polyisoprenoids, such as ethanol, methanol, or acetone, or by adding an acid to the rubber particles. Rubber (a type of polyisoprenoid) can be recovered as solids from the rubber particles by the solidification step. The obtained rubber may be dried if necessary before use.

Thus, according to the first disclosure, by binding a protein expressed from a gene coding for a neryl diphosphate synthase to rubber particles in vitro, it is possible to synthesize a polyisoprenoid in the rubber particles, and therefore it is possible to efficiently produce a polyisoprenoid in a reaction vessel (e.g., a test tube or industrial plant).

Thus, another aspect of the first disclosure relates to a method for synthesizing a polyisoprenoid, which includes binding a protein expressed from a gene coding for a neryl diphosphate synthase to rubber particles in vitro, for example in a reaction vessel (e.g., a test tube or industrial plant).

Here, the step of binding a protein expressed from a gene coding for a neryl diphosphate synthase to rubber particles in vitro is as described above.

Here, neryl diphosphate synthase is known to bind dimethylallyl diphosphate (DMAPP) as a starting substrate and isopentenyl diphosphate (IPP) as a monomer in a cis configuration. The present inventors found that the above-described mutant protein obtained by replacing the helix 3 region by the helix 3 region of a cis-prenyltransferase capable of producing an isoprenoid chain having 35 or greater carbon atoms can use even an allylic diphosphate derivative such as DMAPP whose structure has been partially modified as a starting substrate to synthesize a modified neryl diphosphate and further elongate an isoprenoid chain. Accordingly, the use of the mutant protein enables isoprenoid chain elongation from a non-naturally occurring modified neryl diphosphate and synthesis of a non-naturally occurring polyisoprenoid having a modified initiating terminal. Thus, it is possible to synthesize a polyisoprenoid having an additional function not found in naturally occurring polyisoprenoids. For example, it is possible to produce a polyisoprenoid having a high affinity for filler such as silica or carbon black.

Since neryl diphosphate synthase and a starting substrate interact with each other through magnesium ions at the diphosphate site of the starting substrate, the recognition of the starting substrate is considered to depend on the spatial size of the hydrophobic pocket containing the helix 3 region and the size of the substrate. In the mutant protein in which the helix 3 region has been replaced by the helix 3 region of a cis-prenyltransferase capable of producing an isoprenoid chain having 35 or greater carbon atoms, it is considered that the space within the hydrophobic pocket for recognition of the starting substrate increases so that a starting substrate other than the original starting substrate DMAPP can also enter the hydrophobic pocket and can be used as a substrate.

Specifically, for example, an allylic diphosphate derivative obtained by replacing the methyl group located in the trans position with respect to position 3 of DMAPP by a desired group (—R) may be used instead of DMAPP to synthesize a modified neryl diphosphate in which IPP is bound to the allylic diphosphate derivative as described below, which may then be used as an initiating terminal to further elongate an isoprenoid chain.

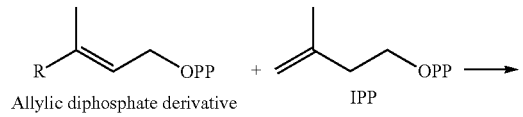
Allylic diphosphate derivative + IPP →

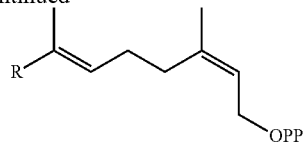

Here, OPP refers to a diphosphate group which has three hydroxy groups bound to a phosphorus atom. A part or all of the hydroxy groups dissociate in an aqueous solution. Herein, the term "OPP" conceptually includes such groups in which a part or all of the hydroxy groups have dissociated.

The substituent R may be, for example, a nitrogen-containing group, an oxygen-containing group, a sulfur-containing group, a silicon-containing group, or a carbon-containing group, examples of which include acetoxy, alkoxy (preferably C1-C3 alkoxy, more preferably methoxy), hydroxy, aryl (preferably phenyl, benzyl, or phenylethyl), alkyl (preferably C1-C5 alkyl, more preferably ethyl), alkoxyalkyl (preferably C2-C10 alkoxyalkyl, more preferably C4-C6 alkoxyalkyl), acetyl, N-alkyl-acetamino (in which the alkyl preferably has 1 to 5 carbon atoms), and azide groups.

From the standpoint of reactivity with the mutant protein, aryl and alkoxyalkyl groups are preferred among these. Moreover, they are also preferred in that the use of a starting substrate having an aryl substituent enables production of a polyisoprenoid having a high affinity for a styrene-butadiene copolymer, an aromatic-containing resin, or the like, while the use of a starting substrate having an alkoxyalkyl substituent enables production of a polyisoprenoid having a high affinity for silica or the like.

Examples of the allylic diphosphate derivative include the compounds represented by the following formulas (A) to (E). From the standpoint of reactivity with the mutant protein, the compounds of formulas (B) and (C) are preferred among these. Moreover, the compounds of formulas (A), (D), and (E) are also preferred in that a naturally occurring cis-prenyltransferase cannot use them as a starting substrate, while the mutant protein can use them a starting substrate.

(A)

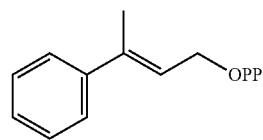

(B)

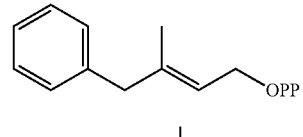

(C)

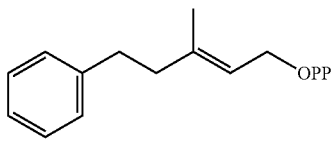

(D)

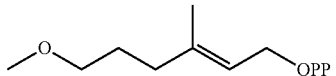

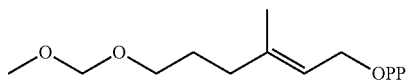

(E)

Allylic diphosphate derivatives such as those of formulas (A) to (E) can be produced from DMAPP by known techniques.

Moreover, when DMAPP or an allylic diphosphate derivative is used as a starting substrate instead of farnesyl diphosphate (FPP), which is a starting substrate for natural polyisoprenoid synthesis, to synthesize a polyisoprenoid having a non-naturally occurring initiating terminal, it is possible to influence the chain length of the polyisoprenoid to be synthesized. Specifically, it is possible to make the chain length longer than that of a polyisoprenoid synthesized using FPP as a starting substrate. Furthermore, the mutant protein may be used to further influence the chain length of the polyisoprenoid to be synthesized.

Herein, the term "polyisoprenoid" is a collective term for polymers formed of isoprene units ($C_5H_8$). Examples of polyisoprenoids include sesterterpenes ($C_{25}$), triterpenes ($C_{30}$), tetraterpenes ($C_{40}$), rubber, and other polymers. Also herein, the term "isoprenoid" refers to a compound containing an isoprene unit ($C_5H_8$), and conceptually includes polyisoprenoids.

(Method for Producing Rubber Product)

The method for producing a rubber product of the first disclosure includes: kneading a polyisoprenoid produced by the method for producing a polyisoprenoid of the first disclosure with an additive to obtain a kneaded mixture; forming a raw rubber product from the kneaded mixture; and vulcanizing the raw rubber product.

The rubber product is not limited as long as it is a rubber product that can be produced from rubber, preferably natural rubber, and examples include pneumatic tires, rubber rollers, rubber fenders, gloves, and medical rubber tubes.

When the rubber product is a pneumatic tire, or in other words when the method for producing a rubber product of the first disclosure is a method for producing a pneumatic tire of the first disclosure, the raw rubber product forming step corresponds to building a green tire from the kneaded mixture, and the vulcanization step corresponds to vulcanizing the green tire. Thus, the method for producing a pneumatic tire of the first disclosure includes: kneading a polyisoprenoid produced by the method for producing a polyisoprenoid with an additive to obtain a kneaded mixture; building a green tire from the kneaded mixture; and vulcanizing the green tire.

<Kneading Step>

In the kneading step, the polyisoprenoid produced by the method for producing a polyisoprenoid is kneaded with an additive to obtain a kneaded mixture.

Any additive may be used, including additives used in the production of rubber products. For example, in the case where the rubber product is a pneumatic tire, examples of the additive include rubber components other than the polyisoprenoid, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

In the kneading step, kneading may be carried out using an open roll mill, a Banbury mixer, an internal mixer, or other rubber kneading machines.

<Raw Rubber Product Forming Step (Green Tire Building Step in the Case of Tire)>

In the raw rubber product forming step, a raw rubber product (green tire in the case of tire) is formed from the kneaded mixture obtained in the kneading step.

The raw rubber product may be formed by any method, including appropriate methods used to form raw rubber products. For example, in the case where the rubber product is a pneumatic tire, the kneaded mixture obtained in the kneading step may be extruded into the shape of a tire component and then formed and assembled with other tire components in a usual manner on a tire building machine to build a green tire (unvulcanized tire).

<Vulcanization Step>

In the vulcanization step, the raw rubber product obtained in the raw rubber product forming step is vulcanized to obtain a rubber product.

The raw rubber product may be vulcanized by any method, including appropriate methods used to vulcanize raw rubber products. For example, in the case where the rubber product is a pneumatic tire, the green tire (unvulcanized tire) obtained in the raw rubber product forming step may be vulcanized by heating and pressing in a vulcanizer to obtain a pneumatic tire.

(Second Disclosure)

(Vector)

The vector of the second disclosure contains a nucleotide sequence in which a gene coding for a neryl diphosphate synthase is functionally linked to a promoter having a promoter activity that drives laticifer-specific gene expression. By introducing such a vector into a plant for transformation, the gene coding for a protein involved in polyisoprenoid biosynthesis in the vector can be expressed specifically in laticifers, thereby enhancing cis-isoprenoid or polyisoprenoid production in the plant. This is probably because, if the expression of an exogenous gene introduced for the purpose of enhancing latex productivity is promoted in sites other than laticifers, a certain load is imposed on the metabolism or latex production of the plant, thereby causing adverse effects.

Herein, "promoter having a promoter activity that drives laticifer-specific gene expression" means that the promoter has activity to control gene expression to cause a desired gene to be expressed specifically in laticifers when the desired gene is functionally linked to the promoter and introduced into a plant. Here, the term "laticifer-specific gene expression" means that the gene is expressed substantially exclusively in laticifers with no or little expression of the gene in sites other than laticifers in plants. Also, "a gene is functionally linked to a promoter" means that the gene sequence is linked downstream of the promoter so that the gene is controlled by the promoter.

The vector of the second disclosure can be prepared by inserting the nucleotide sequence of a promoter having a promoter activity that drives laticifer-specific gene expression and the nucleotide sequence of a gene coding for a neryl diphosphate synthase into a vector commonly known as a plant transformation vector by conventional techniques. Examples of vectors that can be used to prepare the vector of the second disclosure include pBI vectors, binary vectors such as pGA482, pGAH, and pBIG, intermediate plasmids such as pLGV23Neo, pNCAT, and pMON200, and pH35GS containing GATEWAY cassette.

As long as the vector of the second disclosure contains the nucleotide sequence of a promoter having a promoter activity that drives laticifer-specific gene expression and the nucleotide sequence of a gene coding for a neryl diphosphate synthase, it may contain additional nucleotide sequences. In addition to these nucleotide sequences, the vector usually contains vector-derived sequences as well as other sequences such as a restriction enzyme recognition sequence, a spacer sequence, a marker gene sequence, and a reporter gene sequence.

Examples of the marker gene include drug-resistant genes such as a kanamycin-resistant gene, a hygromycin-resistant gene, and a bleomycin-resistant gene. Moreover, the reporter gene is intended to be introduced to determine the expression site in a plant, and examples include a luciferase gene, a β-glucuronidase (GUS) gene, a green fluorescent protein (GFP), and a red fluorescent protein (RFP).

The origin of the gene coding for a neryl diphosphate synthase is not limited, and the gene may be derived from a microorganism, an animal, or a plant, preferably a plant, more preferably the genus *Solanum*. In particular, it is particularly preferably derived from tomato.

Here, the gene coding for a neryl diphosphate synthase and the neryl diphosphate synthase in the second disclosure are as described above for the first disclosure.

As long as the vector of the second disclosure contains the nucleotide sequence of a promoter having a promoter activity that drives laticifer-specific gene expression and the nucleotide sequence of a gene coding for a neryl diphosphate synthase, it may further contain the nucleotide sequences of genes coding for additional proteins.

Examples of the genes coding for additional proteins include those as described above in connection with the first disclosure.

The promoter having a promoter activity that drives laticifer-specific gene expression is preferably at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

Herein, the term "rubber elongation factor (REF)" refers to a rubber particle-associated protein that is bound to rubber particles in the latex of rubber-producing plants such as Hevea *brasiliensis*, and contributes to stabilization of the rubber particles.

The term "small rubber particle protein (SRPP)" refers to a rubber particle-associated protein that is bound to rubber particles in the latex of rubber-producing plants such as Hevea *brasiliensis*.

The term "Hevein 2.1 (HEV2.1)" refers to a protein that is highly expressed in the laticifer cells of rubber-producing plants such as Hevea *brasiliensis*. This protein is involved in coagulation of rubber particles and has antifungal activity.

Moreover, the term "MYC1 transcription factor (MYC1)" refers to a transcription factor that is highly expressed in the latex of rubber-producing plants such as Hevea *brasiliensis* and participates in jasmonic acid signaling. Here, the term "transcription factor" means a protein having activity to increase or decrease, preferably increase, gene transcription. In other words, MYC1 herein is a protein having activity (transcription factor activity) to increase or decrease, preferably increase, the transcription of a gene coding for at least one protein among the proteins involved in jasmonic acid signaling.

(Promoter of Gene Coding for Rubber Elongation Factor (REF))

The origin of the promoter of a gene coding for REF is not limited, but the promoter is preferably derived from a plant, more preferably a rubber-producing plant, still more preferably at least one selected from the group consisting of plants of the genera Hevea, *Sonchus*, *Taraxacum*, and *Parthenium*. In particular, it is further more preferably derived from at least one species of plant selected from the group consisting of Hevea *brasiliensis*, *Sonchus oleraceus*, *Parthenium argentatum*, and *Taraxacum kok-saghyz*, particularly preferably Hevea *brasiliensis*.

The promoter of a gene coding for REF is preferably any one of the following DNAs [A1] to [A3]:
 [A1] a DNA having the nucleotide sequence represented by SEQ ID NO: 3;
 [A2] a DNA which hybridizes under stringent conditions to a DNA having a nucleotide sequence complementary to the nucleotide sequence represented by SEQ ID NO: 3, and which has a promoter activity that drives laticifer-specific gene expression; and
 [A3] a DNA having a nucleotide sequence with at least 60% sequence identity to the nucleotide sequence represented by SEQ ID NO: 3, and having a promoter activity that drives laticifer-specific gene expression.

Here, the term "hybridize" is as described above. Also, the term "stringent conditions" is as described above.

Like the DNAs capable of hybridizing under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 3 is at least 60%, preferably at least 80%, more preferably at least 90%, still more preferably at least 95%, further more preferably at least 98%, particularly preferably at least 99%.

(Promoter of Gene Coding for SRPP)

The origin of the promoter of a gene coding for SRPP is not limited, but the promoter is preferably derived from a plant, more preferably a rubber-producing plant, still more preferably at least one selected from the group consisting of plants of the genera Hevea, *Sonchus*, *Taraxacum*, and *Parthenium*. In particular, it is further more preferably derived from at least one species of plant selected from the group consisting of Hevea *brasiliensis*, *Sonchus oleraceus*, *Parthenium argentatum*, and *Taraxacum kok-saghyz*, particularly preferably Hevea *brasiliensis*.

The promoter of a gene coding for SRPP is preferably any one of the following DNAs [B1] to [B3]:
 [B1] a DNA having the nucleotide sequence represented by SEQ ID NO: 4;
 [B2] a DNA which hybridizes under stringent conditions to a DNA having a nucleotide sequence complementary to the nucleotide sequence represented by SEQ ID NO: 4, and which has a promoter activity that drives laticifer-specific gene expression; and
 [B3] a DNA having a nucleotide sequence with at least 60% sequence identity to the nucleotide sequence represented by SEQ ID NO: 4, and having a promoter activity that drives laticifer-specific gene expression.

Here, the term "hybridize" is as described above. Also, the term "stringent conditions" is as described above.

Like the DNAs capable of hybridizing under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 4 is at least 60%, preferably at least 80%, more preferably at least 90%, still more preferably at least 95%, further more preferably at least 98%, particularly preferably at least 99%.

(Promoter of Gene Coding for HEV2.1)

The origin of the promoter of a gene coding for HEV2.1 is not limited, but the promoter is preferably derived from a plant, more preferably a rubber-producing plant, still more preferably at least one selected from the group consisting of plants of the genera Hevea, *Sonchus, Taraxacum*, and *Parthenium. In particular, it is further more preferably derived from at least one species of plant selected from the group consisting of Hevea brasiliensis, Sonchus oleraceus, Parthenium argentatum*, and *Taraxacum kok-saghyz*, particularly preferably Hevea *brasiliensis.*

The promoter of a gene coding for HEV2.1 is preferably any one of the following DNAs [C1] to [C3]:

[C1] a DNA having the nucleotide sequence represented by SEQ ID NO: 5;

[C2] a DNA which hybridizes under stringent conditions to a DNA having a nucleotide sequence complementary to the nucleotide sequence represented by SEQ ID NO: 5, and which has a promoter activity that drives laticifer-specific gene expression; and

[C3] a DNA which has a nucleotide sequence with at least 60% sequence identity to the nucleotide sequence represented by SEQ ID NO: 5, and which has a promoter activity that drives laticifer-specific gene expression.

Here, the term "hybridize" is as described above. Also, the term "stringent conditions" is as described above.

Like the DNAs capable of hybridizing under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 5 is at least 60%, preferably at least 80%, more preferably at least 90%, still more preferably at least 95%, further preferably at least 98%, particularly preferably at least 99%.

(Promoter of Gene Coding for MYC1)

The origin of the promoter of a gene coding for MYC1 is not limited, but the promoter is preferably derived from a plant, more preferably a rubber-producing plant, still more preferably at least one selected from the group consisting of plants of the genera Hevea, *Sonchus, Taraxacum*, and *Parthenium*. In particular, it is further more preferably derived from at least one species of plant selected from the group consisting of Hevea *brasiliensis, Sonchus oleraceus, Parthenium argentatum*, and *Taraxacum kok-saghyz*, particularly preferably Hevea *brasiliensis.*

The promoter of a gene coding for MYC1 is preferably any one of the following DNAs [D1] to [D3]:

[D1] a DNA having the nucleotide sequence represented by SEQ ID NO: 6;

[D2] a DNA which hybridizes under stringent conditions to a DNA having a nucleotide sequence complementary to the nucleotide sequence represented by SEQ ID NO: 6, and which has a promoter activity that drives laticifer-specific gene expression; and

[D3] a DNA having a nucleotide sequence with at least 60% sequence identity to the nucleotide sequence represented by SEQ ID NO: 6, and having a promoter activity that drives laticifer-specific gene expression.

Here, the term "hybridize" is as described above. Also, the term "stringent conditions" is as described above.

Like the DNAs capable of hybridizing under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 6 is at least 60%, preferably at least 808, more preferably at least 90%, still more preferably at least 95%, further more preferably at least 98%, particularly preferably at least 99%.

Whether the DNA which hybridizes to the above-mentioned DNA under stringent conditions or the DNA having at least 60% sequence identity to the above-mentioned DNA is a DNA having a promoter activity that drives laticifer-specific gene expression may be determined by, for example, conventional techniques such as reporter assays using β-galactosidase, luciferase, green fluorescent protein (GFP), or other protein genes as reporter genes.

Moreover, conventional techniques may be employed to identify the nucleotide sequence of the promoter. For example, a genomic DNA is extracted from a growing plant by the cetyl trimethyl ammonium bromide (CTAB) method, then specific and random primers are designed based on the known nucleotide sequence of the promoter, and a gene including the promoter is amplified by TAIL (thermal asymmetric interlaced)-PCR using the extracted genomic DNA as a template to identify the nucleotide sequence.

The vector of the second disclosure (which contains a nucleotide sequence in which a gene coding for a neryl diphosphate synthase is functionally linked to a promoter having a promoter activity that drives laticifer-specific gene expression) can be introduced into a plant to produce a transgenic plant transformed to express specifically in laticifers a certain protein involved in polyisoprenoid biosynthesis. Moreover, in the transgenic plant in which the certain protein involved in polyisoprenoid biosynthesis is expressed specifically in the laticifers, a certain function (e.g., enzyme activity) newly possessed by the protein in the plant transfected with the vector of the second disclosure is enhanced in the laticifers to enhance a part of the polyisoprenoid biosynthesis pathway. Therefore, it is possible to enhance cis-isoprenoid or polyisoprenoid production in the plant.

The method for preparing the transgenic plant is explained briefly below, though such a transgenic plant can be prepared by conventional methods.

The plant into which the vector of the second disclosure is to be introduced to produce the transgenic plant is not limited, but is preferably a rubber-producing plant, among others, because improved polyisoprenoid productivity and increased polyisoprenoid yield can be expected particularly when a neryl diphosphate synthase is expressed in plants capable of biosynthesizing polyisoprenoids. Among other rubber-producing plants, the plant is more preferably at least one selected from the group consisting of Hevea *brasiliensis, Sonchus oleraceus, Parthenium argentatum*, and *Taraxacum kok-saghyz*, particularly preferably Hevea *brasiliensis.*

The vector of the second disclosure may be introduced into a plant (including plant cells, such as callus, cultured cells, spheroplasts, and protoplasts) by any method that can introduce DNA into plant cells. Examples include methods using *Agrobacterium* (JP S59-140885 A, JP S60-70080 A, WO94/00977), electroporation (JP S60-251887 A), and methods using particle guns (gene guns) (JP 2606856 B, JP 2517813 B). Among these, it is preferred to use a method using *Agrobacterium* (*Agrobacterium* method) to introduce the vector of the second disclosure into a plant to produce a transgenic plant (transgenic plant cells).

Furthermore, the vector of the second disclosure may also be introduced into, for example, an organism (e.g., a microorganism, yeast, animal cell, or insect cell) or a part thereof, an organ, a tissue, a cultured cell, a spheroplast, or a protoplast by any of the above-described DNA introduction methods to produce a cis-isoprenoid or polyisoprenoid.

The transgenic plant (transgenic plant cells) can be produced by the above or other methods. Here, the term "transgenic plant" conceptually includes not only transgenic plant cells produced by the above methods, but also all of their progeny or clones and even progeny plants obtained by passaging the foregoing. Once obtaining transgenic plant cells into which the vector of the second disclosure has been introduced, progeny or clones can be produced from the transgenic plant cells by sexual or asexual reproduction, tissue culture, cell culture, cell fusion, or other techniques. Moreover, the transgenic plant cells, or their progeny or clones may be used to obtain reproductive materials (e.g., seeds, fruits, cuttings, stem tubers, root tubers, shoots, adventitious buds, adventitious embryos, callus, protoplasts), which can then be used to produce the transgenic plant on a large scale.

Techniques to regenerate plants (transgenic plants) from transgenic plant cells are already known; for example, Doi et al. disclose techniques for *eucalyptus* (Japanese Patent Application No. H11-127025), Fujimura et al. disclose techniques for rice (Fujimura et al., (1995), Plant Tissue Culture Lett., vol. 2: p. 74-), Shillito et al. disclose techniques for corn (Shillito et al., (1989), Bio/Technology, vol. 7: p. 581-), Visser et al. disclose techniques for potato (Visser et al., (1989), Theor. Appl. Genet., vol. 78: p. 589-), and Akama et al. disclose techniques for *Arabidopsis thaliana* (Akama et al., (1992), Plant Cell Rep., vol. 12: p. 7-). A person skilled in the art can regenerate plants from the transgenic plant cells with reference to these documents.

Whether a target protein gene is expressed in a regenerated plant may be determined by well-known methods. For example, Western blot analysis may be used to assess the expression of a target protein.

Seeds can be obtained from the transgenic plant, for example, as follows: The transgenic plant is rooted in an appropriate medium and transplanted to water-containing soil in a pot. The plant is grown under proper cultivation conditions to finally produce seeds, which are then collected. Moreover, plants can be grown from seeds, for example, as follows: Seeds obtained from the transgenic plant as described above are sown in water-containing soil and grown under proper cultivation conditions into plants.

According to the second disclosure, by introducing the vector of the second disclosure into a plant, the gene coding for a protein involved in polyisoprenoid biosynthesis, particularly preferably the gene coding for a neryl diphosphate synthase, in the vector can be expressed specifically in the laticifers, thereby enhancing cis-isoprenoid or polyisoprenoid production in the plant. Specifically, a cis-isoprenoid or polyisoprenoid may be produced by culturing, for example, transgenic plant cells produced as described above, callus obtained from the transgenic plant cells, or cells redifferentiated from the callus in an appropriate medium, or by growing, for example, transgenic plants regenerated from the transgenic plant cells, or plants grown from seeds collected from these transgenic plants under proper cultivation conditions.

Thus, another aspect of the second disclosure relates to a method for enhancing cis-isoprenoid production in a plant by introducing the vector of the second disclosure into the plant. Moreover, another aspect of the second disclosure relates to a method for enhancing polyisoprenoid production in a plant by introducing the vector of the second disclosure into the plant.

(Method for Producing Rubber Product)

The method for producing a rubber product of the second disclosure includes: kneading a polyisoprenoid produced by a transgenic plant with an additive to obtain a kneaded mixture, the transgenic plant being produced by introducing the vector of the second disclosure into a plant; forming a raw rubber product from the kneaded mixture; and vulcanizing the raw rubber product.

The rubber product is as described above in connection with the first disclosure.

When the rubber product is a pneumatic tire or, in other words, when the method for producing a rubber product of the second disclosure is a method for producing a pneumatic tire of the second disclosure, the raw rubber product forming step corresponds to building a green tire from the kneaded mixture, and the vulcanization step corresponds to vulcanizing the green tire. Thus, the method for producing a pneumatic tire of the second disclosure includes: kneading a polyisoprenoid produced by a transgenic plant with an additive to obtain a kneaded mixture, the transgenic plant being produced by introducing the vector of the second disclosure into a plant; building a green tire from the kneaded mixture; and vulcanizing the green tire.

<Kneading Step>

In the kneading step, the polyisoprenoid produced by a transgenic plant produced by introducing the vector of the second disclosure into a plant is kneaded with an additive to obtain a kneaded mixture.

The polyisoprenoid produced by a transgenic plant produced by introducing the vector of the second disclosure into a plant can be obtained by harvesting latex from the transgenic plant, and subjecting the latex to the solidification step described below.

Here, the method for harvesting latex from the transgenic plant is not limited, and ordinary harvesting methods may be used. For example, latex may be harvested by collecting the emulsion oozing out from the cuts in the trunk of the plant (tapping), or the emulsion oozing out from the cut roots or other parts of the transgenic plant, or by crushing the cut tissue followed by extraction with an organic solvent.

<Solidification Step>

The harvested latex is subjected to a solidification step. The solidification may be carried out by any method, such as by adding the latex to a solvent that does not dissolve polyisoprenoids, such as ethanol, methanol, or acetone, or by adding an acid to the latex. Rubber (a type of polyisoprenoid) can be recovered as solids from the latex by the solidification step. The obtained rubber may be dried if necessary before use.

Any additive may be used including additives used in the production of rubber products. For example, in the case where the rubber product is a pneumatic tire, examples of the additive include rubber components other than the rubber obtained from the latex, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

In the kneading step, kneading may be carried out using an open roll mill, a Banbury mixer, an internal mixer, or other rubber kneading machines.

<Raw Rubber Product Forming Step (Green Tire Building Step in the Case of Tire)>

The raw rubber product forming step is as described above in connection with the first disclosure.

<Vulcanization Step>

The vulcanization step is as described above in connection with the first disclosure.

EXAMPLES

The present disclosure is specifically described with reference to examples, but the present disclosure is not limited to these examples.

Example 1

[Vector Construction]

Based on the information of a neryl diphosphate synthase gene (NDPS) of tomato (*Solanum lycopersicum*) (SEQ ID NO:1) available in public databases using BLAST, a trNDPS1 gene in which the partial nucleotide sequence (nucleotides 4 to 132 of SEQ ID NO:1) coding for a signal sequence was removed from the region from the start codon to the stop codon was synthesized and prepared using a gene synthesis service.

Here, the amino acid sequence of NDPS encoded by the nucleotide sequence of NDPS represented by SEQ ID NO:1 is given by SEQ ID NO: 2.

trNDPS1 was prepared as described above. The gene was sequenced to identify the full-length nucleotide sequence and amino acid sequence. The nucleotide sequence of trNDPS1 is given by SEQ ID NO: 7. The amino acid sequence of trNDPS1 is given by SEQ ID NO: 8.

The obtained DNA fragment was inserted into pUC57 to prepare pUC57-trNDPS1.

[Transformation of *Escherichia coli*]

*Escherichia coli* DH5×was transformed with the prepared vector, the transformant was cultured on LB agar medium containing ampicillin and X-gal, and *Escherichia coli* cells carrying the introduced target gene were selected by blue/white screening.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

It was confirmed by sequence analysis that there were no mutations in the nucleotide sequence of the gene inserted into the collected plasmid.

[Preparation of Vector for Cell-Free Protein Synthesis]

The insertion of the gene in a cell-free expression system was performed by the seamless ligation cloning extract (SLiCE) method.

A PCR fragment in which the sequence contained in the cell-free expression vector of nucleotides 19 to 21 was added to both terminals of the trNDPS1 gene was obtained by a PCR reaction using pUC57-trNDPS1 acquired in the above [Vector construction] as a template and the primers 1 and 2 described below.

```
Primer 1:
5'-CTGTATTTTCAGGGCGGATATTCTGCTCGTGGACTCAAC-3'

Primer 2:
5'-CAAAACTAGTGCGGCCGCGTCAATATGTGTGTCCACC-3'
```

The cell-free expression vector pEU-E01-His-TEV-MCS-N2 was treated with the restriction enzymes EcoRI and KpnI and purified by gel recovery. The SLICE solution used in the SLICE reaction was prepared as follows.

The cultured *Escherichia coli* DH5×in an amount of 0.3 to 0.4 g was suspended gently in 1.2 mL of 50 mM Tris-HCl (pH 8.0) containing 3% Triton X-100 and incubated for 10 minutes at room temperature. After the incubation, the suspension was centrifuged at 4° C. and 20000×g for two minutes, and the supernatant was collected. To the supernatant was added an equal amount of a 80% glycerol solution to prepare the SLICE solution. The SLICE solution was divided into equal small portions, which were stored at −80° C. until use. The PCR fragment and the restriction enzyme-treated vector were mixed in a ratio of 1:1 to 3:1. To the mixture were added a 10×SLICE buffer (500 µM Tris-HCl (pH 7.5), 100 mM $MgCl_2$, 10 mM ATP, 10 mM DTT) in an amount of 1/10 of the final volume of the reaction system and the SLICE solution in an amount of 1/10 of the final volume of the reaction system, and they were reacted at 37° C. for 15 minutes to prepare pEU-His-N2-trNDPS1.

[Transformation of *Escherichia coli*]

*Escherichia coli* DH5×was transformed with the prepared vector, the transformant was cultured on LB agar medium containing ampicillin and X-gal, and *Escherichia coli* cells carrying the introduced target gene were screened by colony PCR.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

[Preparation of Rubber Particles]

Rubber particles were prepared from Hevea latex by five stages of centrifugation. To 900 mL of Hevea latex was added 100 mL of a 1 M Tris buffer (pH 7.5) containing 20 mM dithiothreitol (DTT) to prepare a latex solution. The latex solution was centrifuged in stages at the following different speeds: 1000×g, 2000×g, 8000×g, 20000×g, and 50000×g. Each stage of centrifugation was carried out for 45 minutes at 4° C. To the rubber particle layer left after the centrifugation at 50000×g was added 3-[(3-cholamidopropyl)dimethylamino]-propanesulfonate (CHAPS) at a final concentration of 0.1 to 2.0×CMC (0.1 to 2.0 times the critical micelle concentration CMC) to wash the rubber particles. After the washing, the rubber particles were collected by ultracentrifugation (40000×g, 4° C., 45 minutes) and re-suspended in an equal amount of a 100 M Tris buffer (pH 7.5) containing 2 mM dithiothreitol (DTT).

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector acquired in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The following amounts of materials were added to a dialysis cup (MWCO 12000, Bio-Teck). A total amount of 60 µL of a reaction solution was prepared according to the protocol of the WEPRO7240H expression kit. To the reaction solution was added 1 to 2 mg of the rubber particles. Separately, 650 μL of SUB-AMIX was added to a No. 2 PP container (Maruemu container).

The dialysis cup was set in the No. 2 PP container, and a protein synthesis reaction was initiated at 26° C. The addition of the mRNA and the replacement of the external dialysis solution (SUB-AMIX) were performed twice after the initiation of the reaction. The reaction was carried out for 24 hours. FIG. 1 shows a schematic diagram illustrating the dialysis process.

[Collection of Reacted Rubber Particles]

The solution in the dialysis cup was transferred to a new 1.5 μL tube, and the reacted rubber particles were collected by ultracentrifugation (40000×g, 4° C., 45 minutes) and re-suspended in an equal amount of a 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as follows.

First, 50 mM Tris-HCl (pH 7.5), 2 mM DTT, 5 mM $MgCl_2$, 15 UM dimethylallyl diphosphate (DMAPP), 100 μM 1-14C isopentenyl diphosphate ([1-14C] IPP, specific activity 5 Ci/mol), and 10 μL of the rubber particle solution were mixed to prepare a reaction solution (100 μL in total), which was then reacted for 16 hours at 30° C.

After the reaction, 200 μL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then very long chain polyisoprenoid (rubber) was further extracted from the aqueous phase with 1 mL of toluene/hexane (1:1), followed by determination of radioactivity. The radioactivity of each phase was determined by 14C counting using a liquid scintillation counter. A higher radioactivity (dpm) indicates a higher production of the very long chain polyisoprenoid (rubber) and a higher rubber synthesis activity.

Table 1 shows the results.

[Measurement of Molecular Weight Distribution of Synthesized Very Long Chain Polyisoprenoid]

Figure 2:
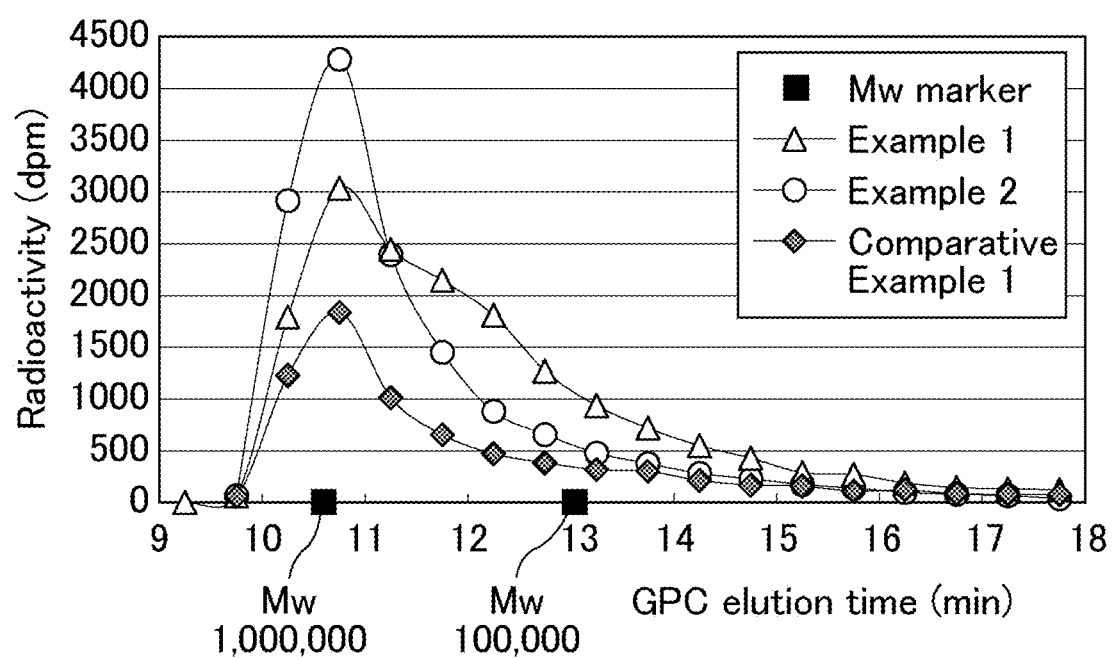
FIG. 2 illustrates a graph of the measured molecular weight distributions of the very long chain polyisoprenoids synthesized in Examples 1 and 2 and Comparative Example 1.

The molecular weight distribution of the very long chain polyisoprenoid (rubber) synthesized as above was measured under the following conditions by radio-HPLC. FIG. 2 shows the results.

HPLC system: a product of GILSON
Column: TSK guard column MP (XL) available from Tosoh
Corporation, TSKgel Multipore Hxr-M (two columns)
Column temperature: 40° C.
Solvent: THF available from Merck
Flow rate: 1 mL/min
UV detection: 215 nm
RI detection: Ramona Star (Raytest GmbH)

Example 2

[Vector Construction]

Based on the information of a neryl diphosphate synthase gene (NDPS) of tomato (*Solanum lycopersicum*) (SEQ ID NO:1) available in public databases using BLAST, a trNDPS1 H3AtCPT4 chimera gene in which the partial nucleotide sequence (nucleotides 4 to 132 of SEQ ID NO:1) coding for a signal sequence was removed from the region from the start codon to the stop codon as in Example 1 and in which the partial nucleotide sequence (nucleotides 439 to 489 of SEQ ID NO:1) coding for a helix 3 region was replaced by the nucleotide sequence coding for the helix 3 region of CPT4 from *Arabidopsis thaliana* (AtCPT4), which is a cis-prenyltransferase capable of producing an isoprenoid chain having 50 or greater carbon atoms was synthesized and prepared using a gene synthesis service.

trNDPS1 H3AtCPT4 chimera was prepared as described above. The gene was sequenced to identify the full-length nucleotide sequence and amino acid sequence. The nucleotide sequence of trNDPS1 H3AtCPT4 chimera is given by SEQ ID NO: 11. The amino acid sequence of trNDPS1 H3AtCPT4 chimera is given by SEQ ID NO: 12.

The obtained DNA fragment was inserted into pUC57 to prepare pUC57-trNDPS1 H3AtCPT4 chimera.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The insertion into the cell-free expression vector pEU-E01-His-TEV-MCS-N2 was performed by the SLICE method as in Example 1 to prepare pEU-His-N2-trNDPS1 H3AtCPT4 chimera.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector pEU-His-N2-trNDPS1 H3AtCPT4 chimera acquired in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1 and re-suspended in an equal amount of a 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

Table 1 shows the results.

[Measurement of Molecular Weight Distribution of Synthesized Very Long Chain Polyisoprenoid]

Figure 7:
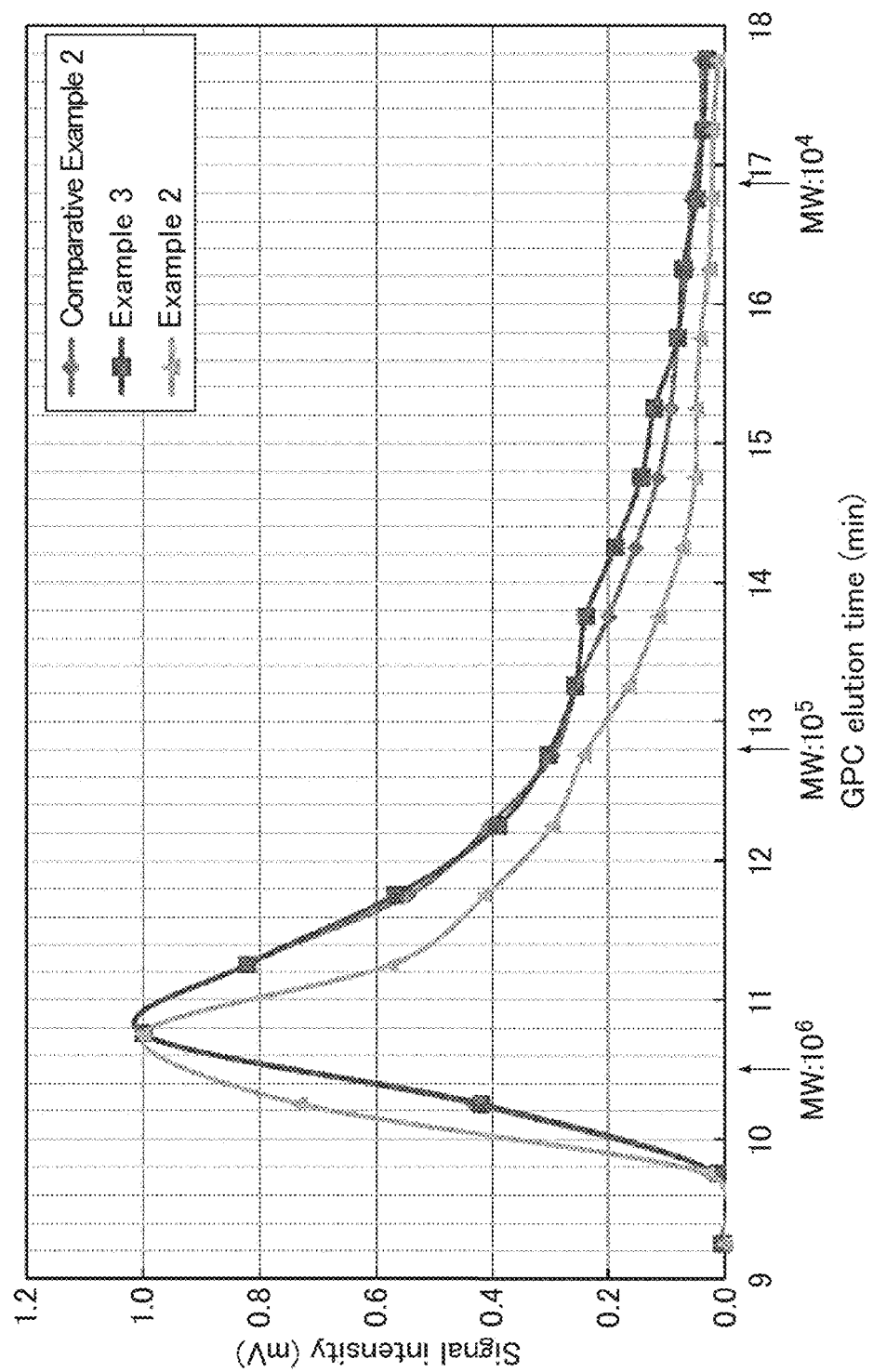
FIG. 7 illustrates a graph of the measured molecular weight distributions of the very long chain polyisoprenoids synthesized in Examples 2 and 3 and Comparative Example 2.

The molecular weight distribution of the very long chain polyisoprenoid synthesized in the above [Measurement of rubber synthesis activity of reacted rubber particles] was measured as in Example 1. FIGS. 2 and 7 show the results.

Comparative Example 1

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the cell-free expression vector pEU-E01-His-TEV-MCS-N2 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1 and re-suspended in an equal amount of a 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

Table 1 shows the results.

[Measurement of Molecular Weight Distribution of Synthesized Very Long Chain Polyisoprenoid]

The molecular weight distribution of the very long chain polyisoprenoid synthesized in the above [Measurement of rubber synthesis activity of reacted rubber particles] was measured as in Example 1. FIG. 2 shows the results.

TABLE 1

| | Bound protein | Radioactivity (dpm) of toluene/hexane layer (rubber extract layer) |
|---|---|---|
| Example 1 | trNDPS1 | 1305.42 |
| Example 2 | trNDPS1 H3AtCPT4 Chimera | 3418.20 |
| Comparative Example 1 | None | 1015.48 |

Table 1 demonstrated that very long chain polyisoprenoid production was able to be more enhanced by binding a neryl diphosphate synthase to rubber particles (Examples 1 and 2) than by binding nothing to rubber particles (Comparative Example 1). Based on this, the increase in very long chain polyisoprenoid production in Example 1 or 2 compared to Comparative Example 1 is considered to correspond to the very long chain polyisoprenoid produced with the involvement of the protein bound to rubber particles. Here, the neryl diphosphate synthase (trNDPS1; Example 1) is an enzyme that catalyzes a reaction to synthesize neryl diphosphate in which isoprene units are linked in a cis configuration using isopentenyl diphosphate and dimethylallyl diphosphate as substrates, and it is presumed that the thus synthesized neryl diphosphate may be used as an initiating terminal to allow a reaction of cis-chain elongation of an isoprenoid compound to proceed on the rubber particles to synthesize a polyisoprenoid. In view of the reaction specificity of the enzymes involved in the reaction, the synthesized polyisoprenoid is therefore considered to be a 100% cis-polyisoprenoid in which no trans configuration is present and all isoprene units are linked in a cis configuration.

Moreover, it is considered that since the mutant neryl diphosphate synthase (trNDPS1 H3AtCPT4 chimera; Example 2) can further catalyze a reaction of cis-chain elongation of an isoprenoid compound using isopentenyl diphosphate and dimethylallyl diphosphate as substrates as compared to neryl diphosphate, the very long chain polyisoprenoid production was further enhanced in Example 2 compared to in Example 1.

Moreover, as shown in FIG. 2, the very long chain polyisoprenoids synthesized in Examples 1 and 2 are long chain rubbers that show the highest peak at a GPC elution time corresponding to a weight average molecular weight (Mw) of about 1,000, 000. Moreover, the very long chain polyisoprenoids synthesized in Examples 1 and 2 are considered to be comparable in molecular weight distribution pattern. It should be noted that since the results in FIG. 2 were not standardized among the samples, the peak heights cannot be used to compare the activities.

Example 3

[Measurement of Rubber Synthesis Activity of Reacted Rubber Particles]

The rubber synthesis activity of the reacted rubber particles collected in Example 2 was measured as follows.

First, 50 mM Tris-HCl (pH 7.5), 2 mM DTT, 5 mM MgCl$_2$, 15 UM farnesyl diphosphate (FPP), 100 µM 1-14C isopentenyl diphosphate ([1-14C] IPP, specific activity: 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (rubber) was further extracted from the aqueous phase with 1 mL of toluene/hexane (1:1), followed by determination of radioactivity. The radioactivity of each phase was determined by 14C counting using a liquid scintillation counter. A higher radioactivity (dpm) indicates a higher production of the very long chain polyisoprenoid (rubber) and a higher rubber synthesis activity.

[Measurement of Molecular Weight Distribution of Synthesized Very Long Chain Polyisoprenoid]

The molecular weight distribution of the very long chain polyisoprenoid synthesized in the above [Measurement of rubber synthesis activity of reacted rubber particles] was measured as in Example 1. FIG. 7 shows the results.

As shown in FIG. 7, in Example 3 using trNDPS1 H3AtCPT4 chimera, a very long chain polyisoprenoid was able to be synthesized even with farnesyl diphosphate (FPP) as a starting substrate, which cannot inherently be used as a starting substrate by NDPS1.

Comparative Example 2

[Extraction of Total RNA from Hevea Latex]

Total RNA was extracted from the latex of Hevea *brasiliensis* by the hot phenol method. To 6 ml of the latex were added 6 mL of a 100 mM sodium acetate buffer and 1 mL of a 10% SDS solution, and then 12 mL of water-saturated phenol pre-heated at 65° C. The mixture was incubated for five minutes at 65° C., agitated in a vortex mixer, and centrifuged at 7000 rpm for 10 minutes at room temperature.

After the centrifugation, the supernatant was transferred to a new tube, 12 mL of a phenol: chloroform (1:1) solution was added, and the mixture was agitated by shaking for two minutes. After the agitation, the resulting mixture was centrifuged again at 7000 rpm for 10 minutes at room temperature. Then, the supernatant was transferred to a new tube, 12 mL of a chloroform: isoamyl alcohol (24:1) solution was added, and the mixture was agitated by shaking for two minutes. After the agitation, the resulting mixture was centrifuged again at 7000 rpm for 10 minutes at room temperature. Then, the supernatant was transferred to a new tube, 1.2 mL of a 3M sodium acetate solution and 13 ml of isopropanol were added, and the mixture was agitated in a vortex mixer. The resulting mixture was incubated for 30 minutes at −20° C. to precipitate total RNA. The incubated mixture was centrifuged at 15000 rpm for 10 minutes at 4° C., and the supernatant was removed to collect a precipitate of total RNA. The collected total RNA was washed twice with 70% ethanol and then dissolved in RNase-free water.

[Synthesis of cDNA from Total RNA]

CDNA was synthesized from the collected total RNA. The CDNA synthesis was carried out using a PrimeScript II 1st strand CDNA synthesis kit (Takara) in accordance with the manual.

[Acquisition of HRT1 Gene from cDNA]

The prepared 1st strand CDNA was used as a template to obtain a HRT1 gene. PCR was performed using a KOD-plus-Neo (Toyobo) in accordance with the manual. The PCR reaction involved 35 cycles with each cycle consisting of 10 seconds at 98° C., 30 seconds at 58° C., and 1 minute at 68° C.

The HRT1 Gene was Obtained Using the Following Primers.

```
Primer 3:
5'-tttggatccgatggaattatacaacggtgagagg-3'

Primer 4:
5'-tttgcggccgcttattttaagtattccttatgtttctcc-3'
```

A HRT1 gene was prepared as described above. The gene was sequenced to identify the full-length nucleotide sequence and amino acid sequence. The nucleotide sequence of HRT1 is given by SEQ ID NO:22. The amino acid sequence of HRT1 is given by SEQ ID NO: 23.

[Vector Construction]

The obtained DNA fragment was subjected to dA addition and then inserted into a pGEM-T Easy vector using a pGEM-T Easy Vector System (Promega) to prepare pGEM-HRT1.

[Transformation of *Escherichia coli*]

*Escherichia coli* DH5×was transformed with the prepared vector, the transformant was cultured on LB agar medium containing ampicillin and X-gal, and *Escherichia coli* cells carrying the introduced target gene were selected by blue/white screening.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection. It was confirmed by sequence analysis that there were no mutations in the nucleotide sequence of the gene inserted in the collected plasmid.

[Preparation of Vector for Cell-Free Protein Synthesis]

The pGEM-HRT1 acquired in the above [Vector construction] was treated with the restriction enzymes Bam HI and Not I and then inserted into a pEU-E01-His-TEV-MCS-N2 cell-free expression vector that had been treated similarly with the restriction enzymes Bam HI and Not I to prepare pEU-His-N2-HRT1.

[Transformation of *Escherichia coli*]

*Escherichia coli* DH5×was transformed with the prepared vector, the transformant was cultured on LB agar medium containing ampicillin and X-gal, and *Escherichia coli* cells carrying the introduced target gene were screened by colony PCR.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector pEU-His-N2-HRT1 acquired in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1 and re-suspended in an equal amount of a 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as follows.

First, 50 mM Tris-HCl (pH 7.5), 2 mM DTT, 5 mM $MgCl_2$, 15 UM farnesyl diphosphate (FPP), 100 UM 1-14C isopentenyl diphosphate ([1-14C] IPP, specific activity: 5 Ci/mol), and 10 μL of the rubber particle solution were mixed to prepare a reaction solution (100 μL in total), which was then reacted for 16 hours at 30° C.

Figure 6:
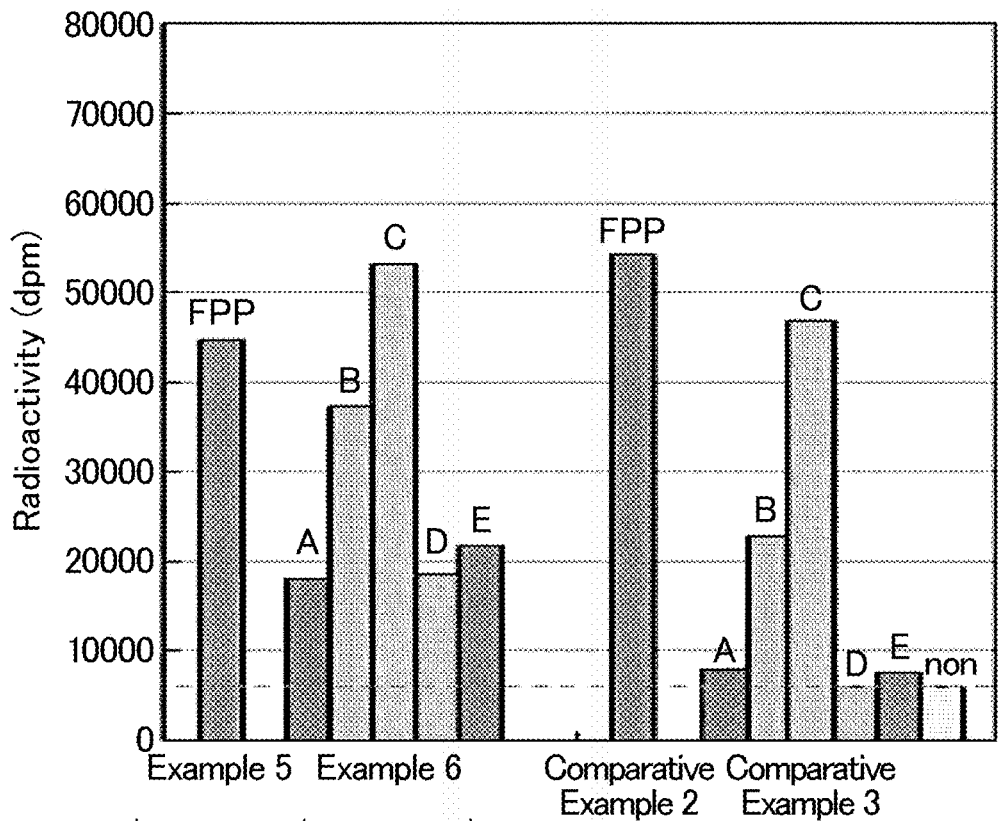
FIG. 6 illustrates a graph of the measured amounts of the very long chain polyisoprenoids synthesized in Examples 5 and 6 and Comparative Examples 2 and 3.

After the reaction, 200 μL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (rubber) was further extracted from the aqueous phase with 1 mL of toluene/hexane (1:1), followed by determination of radioactivity. The radioactivity of each phase was determined by 14C counting using a liquid scintillation counter. A higher radioactivity (dpm) indicates a higher production of the very long chain polyisoprenoid (rubber) and a higher rubber synthesis activity. FIG. 6 shows the results.

[Measurement of Molecular Weight Distribution of Synthesized Very Long Chain Polyisoprenoid]

The molecular weight distribution of the very long chain polyisoprenoid synthesized in the above [Measurement of rubber synthesis activity of reacted rubber particles] was measured as in Example 1. FIG. 7 shows the results.

As shown in FIG. 7, trNDPS1 H3AtCPT4 chimera (Example 3) is considered to synthesize a very long chain polyisoprenoid which is considered to be comparable in molecular weight distribution pattern to that synthesized by the cis-prenyltransferase HRT1 (Comparative Example 2) when FPP, which is a starting substrate for natural very long-chain polyisoprenoid synthesis, is used as a starting substrate. In contrast, when DMAPP is used as a starting substrate (Example 2), the curve more rapidly rises on the high molecular weight side, indicating that the molecular weight of the product is further increased. This suggests that by using as a starting substrate DMAPP or an allylic diphosphate derivative each of which is not a starting substrate for natural very long chain polyisoprenoid synthesis, it is possible to influence the chain length of the polyisoprenoid to be synthesized; specifically, it is possible to make the chain length longer than that of a polyisoprenoid synthesized using as a starting substrate a starting substrate for natural very long chain polyisoprenoid synthesis.

Example 4

[Verification of Binding of Enzyme to Reacted Rubber Particles]

Figure 8:
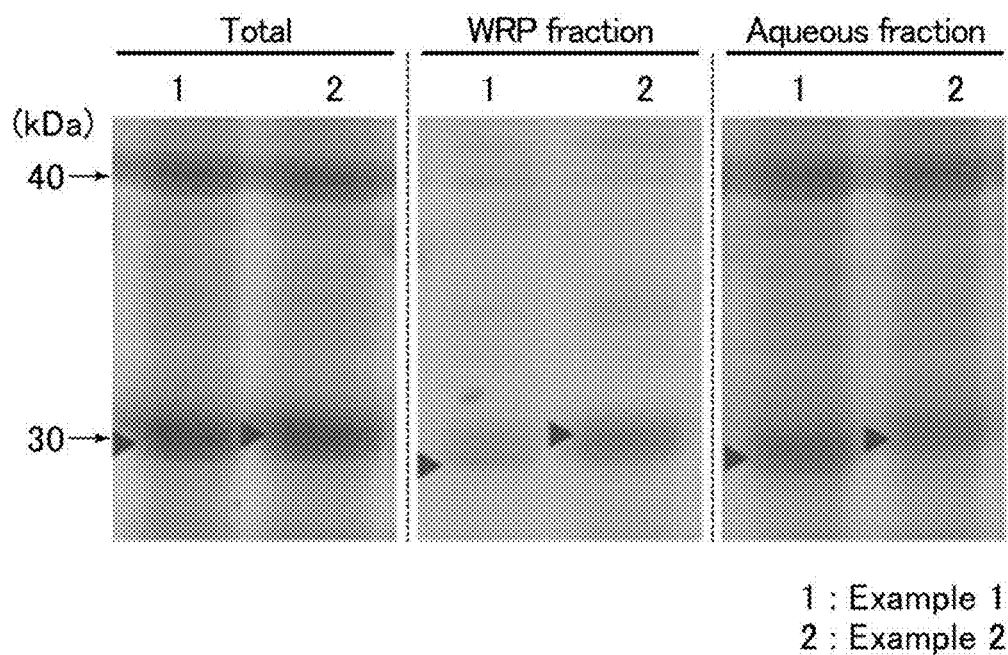
FIG. 8 shows electrophoresis images illustrating the SDS-PAGE test results in Examples 1 and 2.

The verification of binding of the enzyme to the reacted rubber particles collected in Example 1 was performed by SDS-PAGE. FIG. 8 shows the results.

Here, the protein staining was carried out by CBB staining. The SDS-PAGE was carried out using a mini slab gel electrophoresis chamber available from Nihon Eido. The SDS-PAGE separation gel used was a 15% acrylamide gel, and common electrophoresis conditions were used. The marker used was XL-ladder (Broad) available from Apro Science.

[Verification of Binding of Enzyme to Reacted Rubber Particles]

The verification of binding of the enzyme to the reacted rubber particles collected in Example 2 was performed by SDS-PAGE as described above. FIG. 8 shows the results.

In FIG. 8, the "Total" represents the results of electrophoresis of all proteins in a cell-free protein synthesis reaction solution; the "WRP fraction" represents the results of electrophoresis of the proteins present on rubber particles, among the proteins in the reaction solution; and the "Aqueous fraction" represents the results of electrophoresis of the proteins present in the aqueous phase, among the proteins in the reaction solution. As shown in FIG. 8, a comparison of the densities of the bands in lane 1 shows that as for trNDPS1 (Example 1), the ratio of the expressed proteins on rubber particles and in the aqueous phase is such that the amount in the aqueous phase is higher than the amount on rubber particles. In contrast, a comparison of the densities of the bands in lane 2 shows that as for trNDPS1 H3AtCPT4 chimera (Example 2), the ratio of the expressed proteins on rubber particles and in the aqueous phase is such that the amount on rubber particles is higher than the amount in the aqueous phase. This suggests that the binding ability to rubber particles is increased by using, instead of a neryl diphosphate synthase, a mutant protein obtained by replacing the helix 3 region of the neryl diphosphate synthase by the helix 3 region of a cis-prenyltransferase capable of producing an isoprenoid chain having 35 or greater carbon atoms.

Example 5

[Vector Construction]

Based on the information of a neryl diphosphate synthase gene (NDPS) of tomato (*Solanum lycopersicum*) (SEQ ID NO:1) available in public databases using BLAST, a trNDPS1 H3HRT chimera gene in which the partial nucleotide sequence (nucleotides 4 to 132 of SEQ ID NO:1) coding for a signal sequence was removed from the region from the start codon to the stop codon as in Example 1 and in which the partial nucleotide sequence (nucleotides 439 to 489 of SEQ ID NO:1) coding for a helix 3 region was replaced by the nucleotide sequence coding for the helix 3 region of HRT1 from Hevea *brasiliensis*, which is a cis-prenyltransferase that is present on rubber particles and capable of producing an isoprenoid chain having 50 or greater carbon atoms was synthesized and prepared using a gene synthesis service.

trNDPS1 H3HRT chimera was prepared as described above. The gene was sequenced to identify the full-length nucleotide sequence and amino acid sequence. The nucleotide sequence of trNDPS1 H3HRT chimera is given by SEQ ID NO: 18. The amino acid sequence of trNDPS1 H3HRT chimera is given by SEQ ID NO: 19.

The obtained DNA fragment was inserted into pUC57 to prepare pUC57-trNDPS1 H3HRT chimera.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The insertion into the cell-free expression vector pEU-E01-His-TEV-MCS-N2 was performed by the SLICE method as in Example 1 to prepare pEU-His-N2-trNDPS1 H3HRT chimera.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector pEU-His-N2-trNDPS1 H3HRT chimera acquired in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1 and re-suspended in an equal amount of a 100 M Tris buffer (pH 7.5) containing 2 mM dithiothreitol (DTT).

[Verification of Binding of Enzyme to Reacted Rubber Particles]

The verification of binding of the enzyme to the collected reacted rubber particles was performed by SDS-PAGE as in Example 4. The verified binding of the enzyme to rubber particles strongly suggests that a very long chain polyisoprenoid can also be synthesized in Example 5 as in other examples.

[Measurement of Rubber Synthesis Activity of Reacted Rubber Particles]

The rubber synthesis activity of the collected reacted rubber particles was measured as follows.

First, 50 mM Tris-HCl (pH 7.5), 2 mM DTT, 5 mM MgCl$_2$, 15 UM farnesyl diphosphate (FPP), 100 UM 1-14C isopentenyl diphosphate ([1-14C] IPP, specific activity: 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (rubber) was further extracted from the aqueous phase with 1 mL of toluene/hexane (1:1), followed by determination of radioactivity. The radioactivity of each phase was determined by 14C counting using a liquid scintillation counter. A higher radioactivity (dpm) indicates a higher production of the very long chain polyisoprenoid (rubber) and a higher rubber synthesis activity. The results of the determination of radioactivity show that the radioactivity is higher than that in Example 2. This is considered to be because the binding force between the neryl diphosphate synthase and rubber particles is increased due to the helix 3 region that is of the same origin as the rubber particles.

FIG. 6 shows the results.

Figure 3:
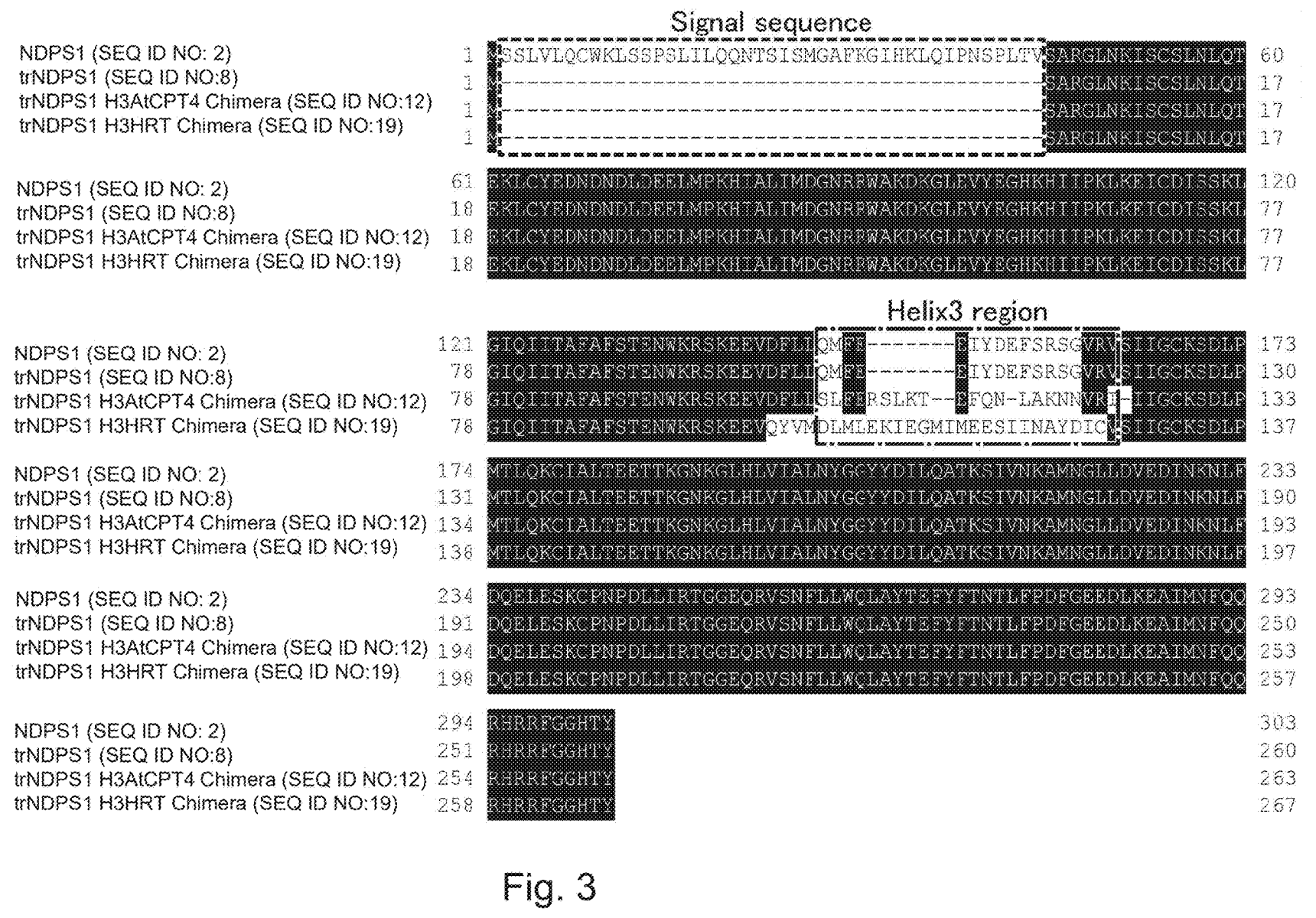
Figure 4:
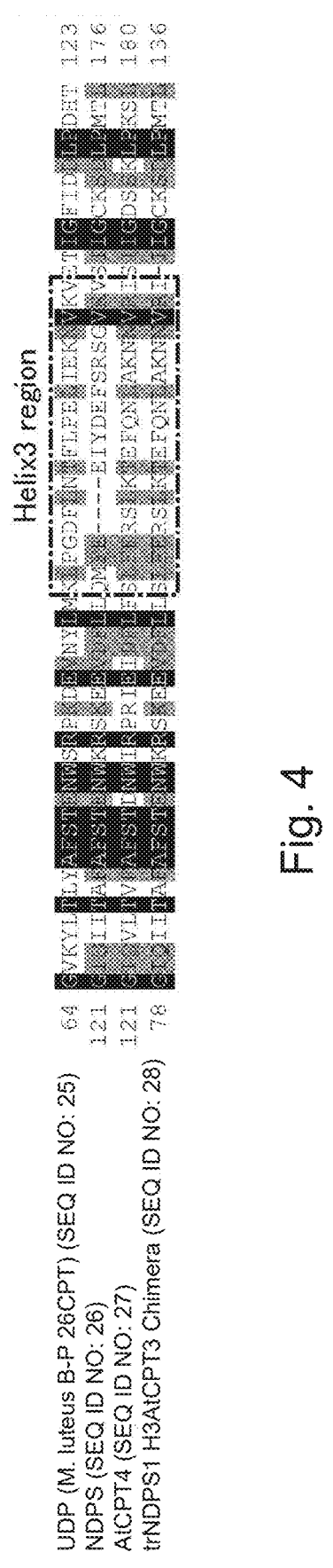

Here, FIG. 3 illustrates the results of multiple sequence alignment of the amino acid sequences of the neryl diphosphate synthases (NDPS (SEQ ID NO: 2), trNDPS1 (SEQ ID NO: 8), trNDPS1 H3AtCPT4 chimera (SEQ ID NO:12), trNDPS1 H3HRT chimera (SEQ ID NO: 19)) used in the examples. In FIG. 3, the signal sequence portion and the helix 3 region are each surrounded by the frame. Moreover, FIG. 4 illustrates the results of multiple sequence alignment of the amino acid sequences of undecaprenyl diphosphate synthase (UPS) from *Micrococcus* (*Micrococcus luteus* B-P 26) (UDP (*M. luteus* B-P 26CPT)), a neryl diphosphate synthase (NDPS (SEQ ID NO: 2), CPT4 from *Arabidopsis thaliana* (AtCPT4), and trNDPS1 H3AtCPT4 chimera (SEQ ID NO:12)). FIG. 4 illustrates the alignment results around the helix 3 region. In FIG. 4, the helix 3 region is surrounded by the frame. The multiple sequence alignment was carried out using software called Genetyx Ver. 11.

The multiple sequence alignment of the cis-prenyltransferases derived from various organisms as shown in FIG. 5, each capable of producing an isoprenoid chain having 35 or greater carbon atoms, was performed. FIG. 5 shows the alignment results around the helix 3 region. In FIG. 5, the helix 3 region is surrounded by the frame. The multiple sequence alignment was carried out using software called Genetyx Ver. 11 as described above.

In FIG. 5, UDP (*M. luteus* B-P 26CPT) corresponds to a selected sequence of positions 75 to 129 of undecaprenyl diphosphate synthase (UPS) from *Micrococcus* (*Micrococcus* (*Micrococcus luteus* B-P 26)).

UPPS (*Escherichia coli*) corresponds to a selected sequence of positions 71 to 125 of undecaprenyl pyrophosphate synthase (UPPS) from *Escherichia coli*.

Srt1 (Yeast CPT) corresponds to a selected sequence of positions 121 to 180 of SRT1 from yeast.

HDS (Human CPT) corresponds to a selected sequence of positions 80 to 137 of HDS from human.

As shown in FIG. 5, the helix 3 region of undecaprenyl diphosphate synthase (UPS) from *Micrococcus* (*Micrococcus luteus* B-P 26) (the amino acid sequence at positions 90 to 110 of undecaprenyl diphosphate synthase (UPS) from *Micrococcus* (*Micrococcus luteus* B-P 26) represented by SEQ ID NO: 15) corresponds to the amino acid sequence at positions 86 to 106 of undecaprenyl pyrophosphate synthase (UPPS) from *Escherichia coli* represented by SEQ ID NO: 14 in the case of undecaprenyl pyrophosphate synthase (UPPS) from *Escherichia coli*, the amino acid sequence at positions 136 to 161 of SRT1 from yeast represented by SEQ ID NO: 16 in the case of SRT1 from yeast, and the amino acid sequence at positions 95 to 118 of HDS from human represented by SEQ ID NO: 17 in the case of HDS from human.

Example 6

[Measurement of Rubber Synthesis Activity of Reacted Rubber Particles]

The rubber synthesis activity of the reacted rubber particles collected in Example 5 was measured as follows.

First, 50 mM Tris-HCl (pH 7.5), 2 mM DTT, 5 mM MgCl$_2$, 15 UM allylic diphosphate derivative, 100 µM 1-14C isopentenyl diphosphate ([1-14C] IPP, specific activity: 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (rubber) was further extracted from the aqueous phase with 1 mL of toluene/hexane (1:1), followed by determination of radioactivity. The radioactivity of each phase was determined by 14C counting using a liquid scintillation counter. A higher radioactivity (dpm) indicates a higher production of the very long chain polyisoprenoid (rubber) and a higher rubber synthesis activity. FIG. 6 shows the results.

Here, the compounds of formulas A to E shown in FIG. 6 were used as the allylic diphosphate derivative.

Comparative Example 3

[Measurement of Rubber Synthesis Activity of Reacted Rubber Particles]

The rubber synthesis activity of the reacted rubber particles collected in Comparative Example 2 was measured as follows.

First, 50 mM Tris-HCl (pH 7.5), 2 mM DTT, 5 mM MgCl$_2$, 15 UM allylic diphosphate derivative, 100 µM 1-14C isopentenyl diphosphate ([1-14C] IPP, specific activity: 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (rubber) was further extracted from the aqueous phase with 1 mL of toluene/hexane (1:1), followed by determination of radioactivity. The radioactivity of each phase was determined by 14C counting using a liquid scintillation counter. A higher radioactivity (dpm) indicates a higher production of the very long chain polyisoprenoid (rubber) and a higher rubber synthesis activity. FIG. 6 shows the results.

Here, the compounds of formulas A to E shown in FIG. 6 were used as the allylic diphosphate derivative.

As shown in FIG. 6, in Example 6 using trNDPS1 H3HRT chimera, a very long chain polyisoprenoid can be synthesized using any of the starting substrates of formulas A to E. In contrast, it is shown that in Comparative Example 3 using the naturally occurring cis-prenyltransferase HRT1, a very long chain polyisoprenoid cannot be synthesized using any of the starting substrates of formulas A, D, and E. These results suggest that the use of a mutant protein obtained by replacing the helix 3 region of a neryl diphosphate synthase by the helix 3 region of a cis-prenyltransferase capable of producing an isoprenoid chain having 35 or greater carbon atoms makes it possible to: use even non-naturally occurring DMAPP whose structure has been partially modified as a starting substrate to synthesize a modified neryl diphosphate and further elongate an isoprenoid chain; to synthesize a non-naturally occurring polyisoprenoid having a modified initiating terminal; and to synthesize a polyisoprenoid having an additional function not found in naturally occurring polyisoprenoids.

[Measurement of Molecular Weight Distribution of Synthesized Very Long Chain Polyisoprenoid]

Figure 9:
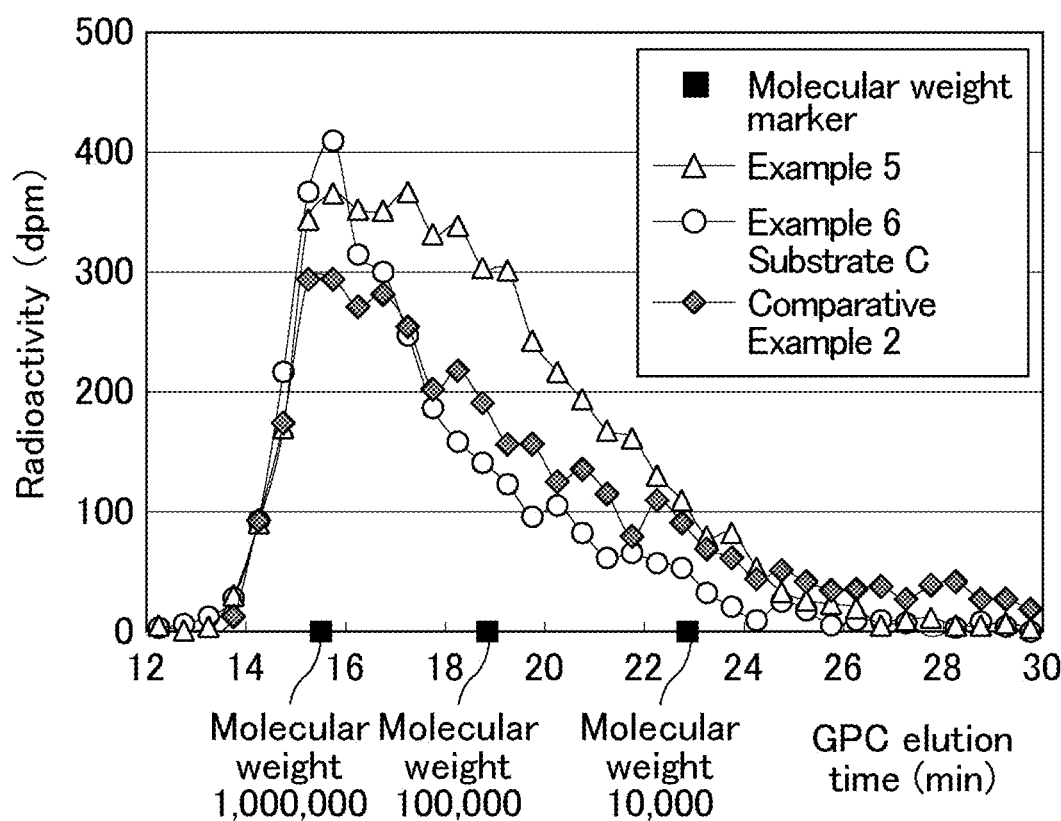
FIG. 9 illustrates a graph of the measured molecular weight distributions of the very long chain polyisoprenoids synthesized in Examples 5 and 6 and Comparative Example 2.

The molecular weight distributions of the very long chain polyisoprenoids (rubbers) synthesized in Comparative Example 2 and Examples 5 and 6 were measured under the following conditions by radio-HPLC. FIG. 9 shows the results.

HPLC system: a product of GILSON
    Column: TSKgel guard column HXL-H and TSKgel GMHXL (two columns) available from Tosoh Corporation
    Column temperature: 40° C.
    Solvent: THE available from Merck
    Flow rate: 1 mL/min
    UV detection: 215 nm
    RI detection: Ramona Star (Raytest GmbH)

As shown in FIG. 9, the very long chain polyisoprenoids synthesized in Examples 5 and 6 are each a long chain rubber that shows the highest peak at a GPC elution time corresponding to a molecular weight of about 1,000, 000. It should be noted that since the results in FIG. 9 were not standardized among the samples, the peak heights cannot be used to compare the activities. Herein, the molecular weight markers used are polystyrene standards.

(Sequence Listing Free Text)
    SEQ ID NO:1: Nucleotide sequence of gene coding for NDPS from tomato
    SEQ ID NO:2: Amino acid sequence of NDPS from tomato
    SEQ ID NO: 3: Nucleotide sequence of promoter of gene coding for rubber elongation factor from Hevea *brasiliensis*
    SEQ ID NO: 4: Nucleotide sequence of promoter of gene coding for small rubber particle protein from Hevea *brasiliensis*
    SEQ ID NO: 5: Nucleotide sequence of promoter of gene coding for Hevien 2.1 from Hevea *brasiliensis*
    SEQ ID NO: 6: Nucleotide sequence of promoter of gene coding for MYC1 transcription factor from Hevea *brasiliensis*
    SEQ ID NO: 7: Nucleotide sequence of gene coding for trNDPS1 from tomato obtained in Example 1
    SEQ ID NO: 8: Amino acid sequence of trNDPS1 from tomato obtained in Example 1
    SEQ ID NO: 9: Primer 1
    SEQ ID NO:10: Primer 2
    SEQ ID NO: 11: Nucleotide sequence of gene coding for trNDPS1 H3AtCPT4 chimera from tomato obtained in Example 2
    SEQ ID NO: 12: Amino acid sequence of trNDPS1 H3AtCPT4 chimera from tomato obtained in Example 2
    SEQ ID NO:13: Amino acid sequence at positions 147 to 167 of CPT4 from *Arabidopsis thaliana* (AtCPT4)
    SEQ ID NO:14: Amino acid sequence at positions 86 to 106 of undecaprenyl pyrophosphate synthase (UPPS) from *Escherichia coli*
    SEQ ID NO:15: Amino acid sequence at positions 90 to 110 of undecaprenyl diphosphate synthase (UPS) from *Micrococcus*
    SEQ ID NO:16: Amino acid sequence at positions 136 to 161 of SRT1 from yeast
    SEQ ID NO:17: Amino acid sequence at positions 95 to 118 of HDS from human
    SEQ ID NO: 18: Nucleotide sequence of gene coding for trNDPS1 H3HRT chimera from tomato obtained in Example 5
    SEQ ID NO:19: Amino acid sequence of trNDPS1 H3HRT chimera from tomato obtained in Example 5
    SEQ ID NO:20: Primer 3
    SEQ ID NO: 21: Primer 4
    SEQ ID NO: 22: Nucleotide sequence of gene coding for HRT1 from Hevea *brasiliensis*
    SEQ ID NO: 23: Amino acid sequence of HRT1 from Hevea *brasiliensis*
    SEQ ID NO:24: Amino acid sequence at positions 102 to 125 of HRT1 from Hevea *brasiliensis*

The invention claimed is:

1. A vector, comprising:
   a promoter having a promoter activity that drives laticifer-specific gene expression; and
   a gene coding for a neryl diphosphate synthase functionally linked to the promoter;
   wherein the promoter having a promoter activity that drives laticifer-specific gene expression is at least one gene selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

2. A transgenic rubber-producing plant into which the vector according to claim 1 has been introduced,
   wherein the rubber-producing plant is at least one selected from the group consisting of Hevea *brasiliensis*, *Sonchus oleraceus*, *Parthenium argentatum*, and *Taraxacum kok-saghyz*.

3. A method for enhancing cis-isoprenoid production in a rubber-producing plant by introducing the vector according to claim 1 into the rubber-producing plant,
   wherein the rubber-producing plant is at least one selected from the group consisting of Hevea *brasiliensis*, *Sonchus oleraceus*, *Parthenium argentatum*, and *Taraxacum kok-saghyz*.

4. A method for enhancing polyisoprenoid production in a rubber-producing plant by introducing the vector according to claim 1 into the rubber-producing plant,
   wherein the rubber-producing plant is at least one selected from the group consisting of Hevea *brasiliensis*, *Sonchus oleraceus*, *Parthenium argentatum*, and *Taraxacum kok-saghyz*.

\* \* \* \* \*

SEQUENCE LISTING

```
<160> NUMBER OF SEQ ID NOS: 32

<210> SEQ ID NO 1
<211> LENGTH: 912
<212> TYPE: DNA
<213> ORGANISM: Solanum lycopersicum

<400> SEQUENCE: 1
atgagttctt tggttcttca atgttggaaa ttatcatctc catctctgat tttacaacaa    60
```

-continued

```
aatacatcaa tatccatggg tgcattcaaa ggtattcata aacttcaaat cccaaattcg      120
cctctgacag tgtctgctcg tggactcaac aagatttcat gctcactcaa cttacaaacc      180
gaaaagcttt gttatgagga taatgataat gatcttgatg aagaacttat gcctaaacac      240
attgctttga taatggatgg taataggaga tgggcaaagg ataagggttt agaagtatat      300
gaaggtcaca acatattat tccaaaatta aaagagattt gtgacatttc ttctaaattg       360
ggaatacaaa ttatcactgc ttttgcattc tctactgaaa attggaaacg atccaaggag      420
gaggttgatt tcttgttgca aatgttcgaa gaaatctatg atgagttttc gaggtctgga      480
gtaagagtgt ctattatagg ttgtaaatcc gacctcccaa tgacattaca aaaatgcata      540
gcattaacag aagagactac aaagggcaac aaaggacttc accttgtgat tgcactaaac      600
tatggtggat attatgacat attgcaagca acaaaaagca ttgttaataa agcaatgaat      660
ggtttattag atgtagaaga tcaacaag aatttatttg atcaagaact tgaaagcaag       720
tgtccaaatc ctgatttact tataaggaca ggaggtgaac aaagagttag taactttttg      780
ttgtggcaat tggcttacac tgaattttac ttcaccaaca cattgtttcc tgattttgga      840
gaggaagatc ttaaagaggc aataatgaac tttcaacaaa ggcatagacg ttttggtgga      900
cacacatatt ga                                                          912
```

<210> SEQ ID NO 2
<211> LENGTH: 303
<212> TYPE: PRT
<213> ORGANISM: Solanum lycopersicum

<400> SEQUENCE: 2

```
Met Ser Ser Leu Val Leu Gln Cys Trp Lys Leu Ser Ser Pro Ser Leu
1               5                   10                  15

Ile Leu Gln Gln Asn Thr Ser Ile Ser Met Gly Ala Phe Lys Gly Ile
            20                  25                  30

His Lys Leu Gln Ile Pro Asn Ser Pro Leu Thr Val Ser Ala Arg Gly
        35                  40                  45

Leu Asn Lys Ile Ser Cys Ser Leu Asn Leu Gln Thr Glu Lys Leu Cys
    50                  55                  60

Tyr Glu Asp Asn Asp Asn Asp Leu Asp Glu Glu Leu Met Pro Lys His
65                  70                  75                  80

Ile Ala Leu Ile Met Asp Gly Asn Arg Arg Trp Ala Lys Asp Lys Gly
                85                  90                  95

Leu Glu Val Tyr Glu Gly His Lys His Ile Ile Pro Lys Leu Lys Glu
            100                 105                 110

Ile Cys Asp Ile Ser Ser Lys Leu Gly Ile Gln Ile Ile Thr Ala Phe
        115                 120                 125

Ala Phe Ser Thr Glu Asn Trp Lys Arg Ser Lys Glu Glu Val Asp Phe
    130                 135                 140

Leu Leu Gln Met Phe Glu Glu Ile Tyr Asp Glu Phe Ser Arg Ser Gly
145                 150                 155                 160

Val Arg Val Ser Ile Ile Gly Cys Lys Ser Asp Leu Pro Met Thr Leu
                165                 170                 175

Gln Lys Cys Ile Ala Leu Thr Glu Glu Thr Thr Lys Gly Asn Lys Gly
            180                 185                 190

Leu His Leu Val Ile Ala Leu Asn Tyr Gly Gly Tyr Tyr Asp Ile Leu
        195                 200                 205

Gln Ala Thr Lys Ser Ile Val Asn Lys Ala Met Asn Gly Leu Leu Asp
```

```
            210                 215                 220
Val Glu Asp Ile Asn Lys Asn Leu Phe Asp Gln Glu Leu Ser Lys
225                 230                 235                 240

Cys Pro Asn Pro Asp Leu Leu Ile Arg Thr Gly Gly Glu Gln Arg Val
                245                 250                 255

Ser Asn Phe Leu Leu Trp Gln Leu Ala Tyr Thr Glu Phe Tyr Phe Thr
            260                 265                 270

Asn Thr Leu Phe Pro Asp Phe Gly Glu Glu Asp Leu Lys Glu Ala Ile
        275                 280                 285

Met Asn Phe Gln Gln Arg His Arg Arg Phe Gly Gly His Thr Tyr
    290                 295                 300

<210> SEQ ID NO 3
<211> LENGTH: 1650
<212> TYPE: DNA
<213> ORGANISM: Hevea brasiliensis

<400> SEQUENCE: 3
gtagtcacag cataagttgg agcaaacaca aaactacagg cctcccaggt tttaaaaaaa      60
aaaaaaaact tttctacgca taaattttcc aagaaaaata ttttgagga ataatttatt     120 tttattgttc tgttaaaatc tgaaaataaa gaaaaattac ttcctaatgg ttcaaggaaa     180
aaataataat tttatttttg tttataatat tatgaaaata tttaaattat aaaactttaa     240
tttttatttt tttattgtga aatgtataaa aaatacataa aataataaaa ttgtgtttta     300
gccatcctgg ctgttgaggc cgcaaggccc gcaagcagta gccggtaaag gaaaaaccag     360
gggcaatatt tttgcagggt tttttttttt tttttctttt aaaagtaaag aacgtatgta     420
tgagtcttaa agatagtaat tttaatagag tctttgatct tatataattc tcacacattt     480
ttacaatctg atgtggaatc ctaaagtact aactcgtgtc tatgcccatc actcgcaaac     540
ttcaatcagg atcacatcat ggactctcat tttttctttg ttttcactta agtgattaat     600 tttcttttg tcaaaggtaa agaatataca cacatattag aaacaggatt agataattat     660 aaaaaagga taattttaat gaattttta attctatata attcattcac acgtactttc      720
accgcttaat atgtgatatg aaggaattta gccctaattt ggttaagaat taatataaat     780
taaaattata ttgtattaga ttaaattaaa ataaaaatat taaattaatt ttttagaaaa     840
aattaaaatt gatcttgaac caaactcaaa taaagttaat ttgatccctt catttttttt     900
ttattttaat gaaatttaa attgagatct tgtaattttg gaagccattt aaatattatc     960
gatttgctaa taattatgct gaatgtaatt taatggtaaa gaaaataaat aataaaaag    1020 atacatttaa tttaatttaa tttatatatt ttttatttc aaaaaaattt aaaaggaac    1080 agattgttaa atctttattt ttttaattaa attaaattta attgagtctc aaatataata    1140
ttttataatc ttaaaaataa ttttaatatt actgatttaa attatagat ttaatttaaa    1200 aatttttaaa agtaaagaaa ataattaaga ttttaatttt taagtcgcac gtgattttga    1260 atttaattt ttaaaaacaa agactaactt atttttttat aatttattaa gaaaatcatg    1320
aaaatcccca ttctaaatcg acttctggaa ctgggatgat gcgtttgctt tgcgatactc    1380
catgtgcttt acttacccca taaggatcat gcgcgaatca cgatagaacc aatacaacag    1440
caacacgttt acacgctcct tttcttaaca gctggcctgc cattcccacg aatttccatc    1500
tataagtaga gaggtttggt tttagcatca aaccataatc ggttgatagc ctccatcagc    1560
gttttcagaa aggcgggttt cttttttgaa acttaagcga ctgcgttttg aattttgatc    1620
```

```
ttccattttt gcaaaaggaa atcttcgatt                                          1650

<210> SEQ ID NO 4
<211> LENGTH: 919
<212> TYPE: DNA
<213> ORGANISM: Hevea brasiliensis

<400> SEQUENCE: 4
aaccgtccac caatctttga gttccagtga gtcatctact ggttgcttga cagatccatc           60
aataaaacca tatttctttt tggcccgtaa tgcagtcagc atagctcgcg cccattcttc          120
gtaattctcg cccttcaact gaacttgggt aatcaagtta tctgggttgt cattcgaatt          180
cagtgtttaa gaactaaaag ttttcttccc tgatccagaa ctctcatttt tcttttcatc          240
aaccatggct ctgataccat gtaaaaaaac taagaaattt tggaataaga attcttatct          300
ttattgcccc agaaataaaa tatatatata aaaaaattac agctaacaaa taggtcccta          360
atcaagctaa actaccaaaa ttgtatcaaa gtcatacaac aaaaggtaaa aacagatatg          420
cacacaaaaa ttcctaaaca aatgccctaa ataaatacaa aataagtgac agctaacagc          480
tgcatttcca ataattaatt taactaataa aatttataat cttaaaaata attttaatat          540
tattgaatta aaatttataa ataaaattaa cactgttaaa attaaaagaa aattattaag          600
atttgaattt ttaagcggtt atttaatttt gaaaacaag gctaactttt tttttatat          660 aatttactaa aaaattcatg aatgaaaaaa aaaatccat aagtaaactt accccatacg          720
ggttatgcac gctaaaccaa taaaacagaa acacgtttat acactcgttt tcatttccat          780
ctataaatag agagatttgt ttttagtttt aaaccataat cagttgatag cttccacagt          840
gttttccgaa aggcaaatct ttttcaaac ttcagcgact gcgttttgaa tttgtgattt          900
ttaaaggaaa ttttcaatt                                                       919

<210> SEQ ID NO 5
<211> LENGTH: 1680
<212> TYPE: DNA
<213> ORGANISM: Hevea brasiliensis

<400> SEQUENCE: 5
ggctacctta ttgggaacta ccaatttgtg gattgtggtg attgaattaa ctaataagca           60
actgaatgtt aatttccaga ataagaaaac ttgctgattg taatctcaag ttctagagtg          120
aaaataaaga taattatata aaatatatgg aaattattat cctagaggaa attttatttt          180
tttttaaatt aataaaattt ttgtaattaa aaattttacg aaaaaaaatc taataaaata          240
aatttatgta aaattacttt attttttata ataaaataat tacattatgt atgaaactaa          300
gtaatcatag aatatatata tatattattt agtttatgtg tcaaatataa tagattaata          360
ttttctttat tattttttcaa aataattttc atgtcaaccc aattaaataa atatccaact          420 aattttttt ttaaatattt ttatttcaca gagaataatt tgtatataaa aataatttt          480 cataaaaata tttttatta tttaatttta acattaatta atggtacgtg ttcatattat          540
atatgaataa tattttata ttttaataaa attatcaaag ttgagaaaat gatttgctct          600
tttaagttct ctcttaaaaa agaaagtcat ttttcttaaa aataatttaa tttctctttg          660
actaaaatat ttttgttaa ttattttttt aatactccaa acacaaaaaa tgtgaaaaaa          720
aaaatatttt ccacgacaca aacaaacaga attttagcca atcaattagc gcaattttca          780 actccccgc ctcctaaagg ctggactggt gttgttcctg gaggctgata tcctaagcag          840
gtttctggat ttgcactgat tccatgatgg ttgaggcaag agggtatttc taatgagttt          900
```

```
ttatttagcc ctcttggttg ttgcctgcca ctggaaatca ccatggaaac atatatgaag    960
tcaaatgaca attttattt tttaaatttt ctgagagtga ggaaatgaat aagaagaatt   1020 tgttatttt ctttaaagtc gtgttacttt tacataatat attaagtcaa atttatcgac   1080
tcagtgaaaa taatttatat tttataaata agaaaaatct tgttatataa tttaatataa   1140 atttatatc tttttttttt caaggaaata aatttatat cttgatgata agatagagat   1200
aagatcgagt taacccttgc gttaattgga tgtttaaatg cttaatgcat ggctaaggaa   1260
attaatgtct aaaataacag aaatgagaaa aataaatgaa gggtgaaaaa taaataaaac   1320
ctggccctat gctctatatt ggggatggag tgggagccac ctaatgtgtc agtgttcatc   1380
ttcgaacaac gactcgattc aaagcacacc catgaagccg cttcacatca tccctttgaa   1440
actttccacc ctaatcagct atcacacgat ctactttcca atctcatcaa cgctccaaat   1500
ctcaccacca ttcagtccac tttcacttcc tccttgtcct aatcatcttt aatccatcgg   1560
ggtattatgg taattacatg atcaagtctc tctgctataa ataaagccaa gtgagcttag   1620
ctcatcatca catcatttgc ataccagaaa atcaagaatt gggaagaaat gggaagagtt   1680
```

<210> SEQ ID NO 6
<211> LENGTH: 1610
<212> TYPE: DNA
<213> ORGANISM: Hevea brasiliensis

<400> SEQUENCE: 6

```
taccagctat gattcacctc tagtgatatt gattttatta aaaattaagg caatgatgaa     60
tttctttttg aaaaaatcat ttaagattca agagggagat acagtgatgt cgttattttt    120
taattttatg taagtaaaat tcgtcaatca ttcatcaaag ttaactgcgt gctaaataat    180
ttaaaaatta ttgttttttta ttttgaaaa ttataataaa attcatttgt tttaataatt    240
aggttcttag tttataattt ttttatttta aatttaagta tttatgatta attctgattt    300
aatttctgat aattttaaaa ttaaaattat ttgattctta caattttta acaatcattg    360 ttttagacca atctcaaagt aaatgtttca cacgttacaa gggtgcaaaa tgattggacg    420
gtgacagaaa cagtaaatat tatgaattta attgttgcca tgggctgcta aattcaaagg    480
gtcatcatta cgtgattctc gatttacgaa aaaaaaaag tattttcata tatatatgta    540
tatacacaca cacatcatgc aaaatattta gttaataatt ttccaaaatt aaaacttttt    600
tttatagcat acaattaaaa tgttaaattc aattaaaaaa gtgaaaataa aaatataatt    660
ttttacataa aaaatataaa ttttatataa ttattagtga gaatatatat tactagattt    720
aaaatatact gaataaccac tcgcttttta attggttata gtgattaatt aagaatttt    780 tttatctaaa tttattaagt gatccaacaa atttttgaact attatataag tttataaaat    840
tttgattctc cattctacat ttttaaattt tcatttttta tattatgaaa atatatacat    900
aaaaaaatta attaaactag agttaattgt cagaatgaat ctctagtaaa attttctctg    960
attaaaaaat aaatttcata aattatccca ctaaactttt gtcatgtgat catgtcccca   1020
ataaaatttg attttattat aattggcaac tcgatgtcta acctgcgagt aattatacac   1080
catccccatg atacctccat gatttcaagt gtcaaagtat gttttaatga gaaattatta   1140
ggttaactca atgtatatac attatttttt ataattatgt gaaattaatt ctcataatta   1200
tataggacac atacttcgtc cacttatttt ttagaaaaaa agcattatttt tttagcactt   1260 tcaatgtaac taataattaa cggttttta catgtaagta taattgaata ttataaaacg   1320
```

| cattaataca tatatatgca tgattcttgt taatttacca ttctacgtag aatattccat | 1380 |
| atagaatcaa tgctttatta tataataatt tctgctacat aataagaggc tttcatttcc | 1440 |
| tttgtcttta aataacccca agtctcactt gtaaaccaac gtcgctcatt tatccctctt | 1500 |
| accctgtccc tctccaactc tcaaactttc tggaattcca tagattgtgg aaactctcta | 1560 |
| gctaaaccaa aaaacagaaa agaacataca aaattgaaat actaaggtgc | 1610 |

<210> SEQ ID NO 7
<211> LENGTH: 783
<212> TYPE: DNA
<213> ORGANISM: Solanum lycopersicum

<400> SEQUENCE: 7

| atgtctgctc gtggactcaa caagatttca tgctcactca acttacaaac cgaaaagctt | 60 |
| tgttatgagg ataatgataa tgatcttgat gaagaactta tgcctaaaca cattgctttg | 120 |
| ataatggatg gtaataggag atgggcaaag gataagggtt tagaagtata tgaaggtcac | 180 |
| aaacatatta ttccaaaatt aaaagagatt tgtgacattt cttctaaatt gggaatacaa | 240 |
| attatcactg cttttgcatt ctctactgaa aattggaaac gatccaagga ggaggttgat | 300 |
| ttcttgttgc aaatgttcga agaaatctat gatgagtttt cgaggtctgg agtaagagtg | 360 |
| tctattatag gttgtaaatc cgacctccca atgacattac aaaaatgcat agcattaaca | 420 |
| gaagagacta caagggcaa caaggacttt caccttgtga ttgcactaaa ctatggtgga | 480 |
| tattatgaca tattgcaagc aacaaaaagc attgttaata agcaatgaa tggtttatta | 540 |
| gatgtagaag atatcaacaa gaatttattt gatcaagaac ttgaaagcaa gtgtccaaat | 600 |
| cctgatttac ttataaggac aggaggtgaa caaagagtta gtaactttt gttgtggcaa | 660 |
| ttggcttaca ctgaatttta cttccaccaac acattgtttc ctgattttgg agaggaagat | 720 |
| cttaaagagg caataatgaa ctttcaacaa aggcatagac gttttggtgg acacacatat | 780 |
| tga | 783 |

<210> SEQ ID NO 8
<211> LENGTH: 260
<212> TYPE: PRT
<213> ORGANISM: Solanum lycopersicum

<400> SEQUENCE: 8

Met Ser Ala Arg Gly Leu Asn Lys Ile Ser Cys Ser Leu Asn Leu Gln
1               5                   10                  15

Thr Glu Lys Leu Cys Tyr Glu Asp Asn Asp Asn Asp Leu Asp Glu Glu
            20                  25                  30

Leu Met Pro Lys His Ile Ala Leu Ile Met Asp Gly Asn Arg Arg Trp
        35                  40                  45

Ala Lys Asp Lys Gly Leu Glu Val Tyr Glu Gly His Lys His Ile Ile
    50                  55                  60

Pro Lys Leu Lys Glu Ile Cys Asp Ile Ser Ser Lys Leu Gly Ile Gln
65                  70                  75                  80

Ile Ile Thr Ala Phe Ala Phe Ser Thr Glu Asn Trp Lys Arg Ser Lys
                85                  90                  95

Glu Glu Val Asp Phe Leu Leu Gln Met Phe Glu Glu Ile Tyr Asp Glu
            100                 105                 110

Phe Ser Arg Ser Gly Val Arg Val Ser Ile Ile Gly Cys Lys Ser Asp
        115                 120                 125

Leu Pro Met Thr Leu Gln Lys Cys Ile Ala Leu Thr Glu Glu Thr Thr

```
                130               135               140
Lys Gly Asn Lys Gly Leu His Leu Val Ile Ala Leu Asn Tyr Gly Gly
145                 150                 155                 160

Tyr Tyr Asp Ile Leu Gln Ala Thr Lys Ser Ile Val Asn Lys Ala Met
                165                 170                 175

Asn Gly Leu Leu Asp Val Glu Asp Ile Asn Lys Asn Leu Phe Asp Gln
                180                 185                 190

Glu Leu Glu Ser Lys Cys Pro Asn Pro Asp Leu Leu Ile Arg Thr Gly
            195                 200                 205

Gly Glu Gln Arg Val Ser Asn Phe Leu Leu Trp Gln Leu Ala Tyr Thr
        210                 215                 220

Glu Phe Tyr Phe Thr Asn Thr Leu Phe Pro Asp Phe Gly Glu Glu Asp
225                 230                 235                 240

Leu Lys Glu Ala Ile Met Asn Phe Gln Gln Arg His Arg Arg Phe Gly
                245                 250                 255

Gly His Thr Tyr
            260
```

<210> SEQ ID NO 9
<211> LENGTH: 39
<212> TYPE: DNA
<213> ORGANISM: Artificial Sequence
<220> FEATURE:
<223> OTHER INFORMATION: PRIMER-1

<400> SEQUENCE: 9
ctgtattttc agggcggata ttctgctcgt ggactcaac                39

<210> SEQ ID NO 10
<211> LENGTH: 37
<212> TYPE: DNA
<213> ORGANISM: Artificial Sequence
<220> FEATURE:
<223> OTHER INFORMATION: PRIMER-2

<400> SEQUENCE: 10
caaaactagt gcggccgcgt caatatgtgt gtccacc                  37

<210> SEQ ID NO 11
<211> LENGTH: 792
<212> TYPE: DNA
<213> ORGANISM: Solanum lycopersicum

<400> SEQUENCE: 11
atgtctgctc gtggactcaa caagatttca tgctcactca acttacaaac cgaaaagctt    60
tgttatgagg ataatgataa tgatcttgat gaagaactta tgcctaaaca cattgctttg   120
ataatggatg gtaataggag atgggcaaag gataagggtt tagaagtata tgaaggtcac   180
aaacatatta ttccaaaatt aaagagagatt tgtgacattt cttctaaatt gggaatacaa   240
attatcactg cttttgcatt ctctactgaa aattggaaac gatccaagga ggaggttgat   300
ttcttgttga gtttatttga gagatcactc aaaacagaat tcagaacttt agccaagaac   360
aatgttcgga taattatagg ttgtaaatcc gacctcccaa tgacattaca aaaatgcata   420
gcattaacag aagagactac aaagggcaac aaaggacttc accttgtgat tgcactaaac   480
tatggtggat attatgacat attgcaagca acaaaaagca ttgttaataa agcaatgaat   540
ggtttattag atgtagaaga tatcaacaag aattatttg atcaagaact tgaaagcaag   600
tgtccaaatc ctgatttact tataaggaca ggaggtgaac aaagagttag taacttttg   660

```
ttgtggcaat tggcttacac tgaattttac ttcaccaaca cattgtttcc tgattttgga    720
gaggaagatc ttaaagaggc aataatgaac tttcaacaaa ggcatagacg ttttggtgga    780
cacacatatt ga                                                         792
```

<210> SEQ ID NO 12
<211> LENGTH: 263
<212> TYPE: PRT
<213> ORGANISM: Solanum lycopersicum

<400> SEQUENCE: 12

```
Met Ser Ala Arg Gly Leu Asn Lys Ile Ser Cys Ser Leu Asn Leu Gln
1               5                   10                  15

Thr Glu Lys Leu Cys Tyr Glu Asp Asn Asp Asn Leu Asp Glu Glu
            20                  25                  30

Leu Met Pro Lys His Ile Ala Leu Ile Met Asp Gly Asn Arg Arg Trp
        35                  40                  45

Ala Lys Asp Lys Gly Leu Glu Val Tyr Glu Gly His Lys His Ile Ile
50                  55                  60

Pro Lys Leu Lys Glu Ile Cys Asp Ile Ser Ser Lys Leu Gly Ile Gln
65                  70                  75                  80

Ile Ile Thr Ala Phe Ala Phe Ser Thr Glu Asn Trp Lys Arg Ser Lys
                85                  90                  95

Glu Glu Val Asp Phe Leu Leu Ser Leu Phe Glu Arg Ser Leu Lys Thr
            100                 105                 110

Glu Phe Gln Asn Leu Ala Lys Asn Asn Val Arg Ile Ile Ile Gly Cys
        115                 120                 125

Lys Ser Asp Leu Pro Met Thr Leu Gln Lys Cys Ile Ala Leu Thr Glu
130                 135                 140

Glu Thr Thr Lys Gly Asn Lys Gly Leu His Leu Val Ile Ala Leu Asn
145                 150                 155                 160

Tyr Gly Gly Tyr Tyr Asp Ile Leu Gln Ala Thr Lys Ser Ile Val Asn
                165                 170                 175

Lys Ala Met Asn Gly Leu Leu Asp Val Glu Asp Ile Asn Lys Asn Leu
            180                 185                 190

Phe Asp Gln Glu Leu Glu Ser Lys Cys Pro Asn Pro Asp Leu Leu Ile
        195                 200                 205

Arg Thr Gly Gly Glu Gln Arg Val Ser Asn Phe Leu Leu Trp Gln Leu
210                 215                 220

Ala Tyr Thr Glu Phe Tyr Phe Thr Asn Thr Leu Phe Pro Asp Phe Gly
225                 230                 235                 240

Glu Glu Asp Leu Lys Glu Ala Ile Met Asn Phe Gln Gln Arg His Arg
                245                 250                 255

Arg Phe Gly Gly His Thr Tyr
            260
```

<210> SEQ ID NO 13
<211> LENGTH: 21
<212> TYPE: PRT
<213> ORGANISM: Arabidopsis thaliana

<400> SEQUENCE: 13

```
Ser Leu Phe Glu Arg Ser Leu Lys Thr Glu Phe Gln Asn Leu Ala Lys
1               5                   10                  15

Asn Asn Val Arg Ile
            20
```

<210> SEQ ID NO 14
<211> LENGTH: 21
<212> TYPE: PRT
<213> ORGANISM: Escherichia coli

<400> SEQUENCE: 14

Glu Leu Phe Val Trp Ala Leu Asp Ser Glu Val Lys Ser Leu His Arg
1               5                   10                  15

His Asn Val Arg Leu
            20

<210> SEQ ID NO 15
<211> LENGTH: 21
<212> TYPE: PRT
<213> ORGANISM: Micrococcus luteus

<400> SEQUENCE: 15

Lys Leu Pro Gly Asp Phe Leu Asn Thr Phe Leu Pro Glu Leu Ile Glu
1               5                   10                  15

Lys Asn Val Lys Val
            20

<210> SEQ ID NO 16
<211> LENGTH: 26
<212> TYPE: PRT
<213> ORGANISM: Saccharomyces cerevisiae

<400> SEQUENCE: 16

Asn Leu Phe Thr Val Lys Leu Asp Glu Phe Ala Lys Arg Ala Lys Asp
1               5                   10                  15

Tyr Lys Asp Pro Leu Tyr Gly Ser Lys Ile
            20                  25

<210> SEQ ID NO 17
<211> LENGTH: 24
<212> TYPE: PRT
<213> ORGANISM: Homo sapiens

<400> SEQUENCE: 17

Asp Leu Ala Arg Gln Lys Phe Ser Arg Leu Met Glu Glu Lys Glu Lys
1               5                   10                  15

Leu Gln Lys His Gly Val Cys Ile
            20

<210> SEQ ID NO 18
<211> LENGTH: 804
<212> TYPE: DNA
<213> ORGANISM: Solanum lycopersicum

<400> SEQUENCE: 18
atgtctgctc gtggactcaa caagatttca tgctcactca acttacaaac cgaaaagctt      60
tgttatgagg ataatgataa tgatcttgat gaagaactta tgcctaaaca cattgctttg     120
ataatggatg gtaataggag atgggcaaag gataagggtt tagaagtata tgaaggtcac     180
aaacatatta ttccaaaatt aaaagagatt tgtgacattt cttctaaatt gggaatacaa     240
attatcactg cttttgcatt ctctactgaa aattggaaac gatccaagga ggaggttcag     300
tacgtaatgg atctaatgct ggagaagatt gaagggatga tcatggaaga agtatcatc     360 aatgcatatg atatttgcgt atctattata ggttgtaaat ccgacctccc aatgacatta     420

```
caaaaatgca tagcattaac agaagagact acaaagggca acaaaggact tcaccttgtg    480
attgcactaa actatggtgg atattatgac atattgcaag caacaaaaag cattgttaat    540
aaagcaatga atggtttatt agatgtagaa gatatcaaca agaatttatt tgatcaagaa    600
cttgaaagca agtgtccaaa tcctgattta cttataagga caggaggtga acaaagagtt    660
agtaactttt tgttgtggca attggcttac actgaatttt acttcaccaa cacattgttt    720
cctgattttg gagaggaaga tcttaaagag gcaataatga actttcaaca aaggcataga    780
cgttttggtg gacacacata ttga                                           804
```

<210> SEQ ID NO 19
<211> LENGTH: 267
<212> TYPE: PRT
<213> ORGANISM: Solanum lycopersicum

<400> SEQUENCE: 19

```
Met Ser Ala Arg Gly Leu Asn Lys Ile Ser Cys Ser Leu Asn Leu Gln
1               5                   10                  15

Thr Glu Lys Leu Cys Tyr Glu Asp Asn Asp Asn Leu Asp Glu Glu
            20                  25                  30

Leu Met Pro Lys His Ile Ala Leu Ile Met Asp Gly Asn Arg Arg Trp
        35                  40                  45

Ala Lys Asp Lys Gly Leu Glu Val Tyr Glu Gly His Lys His Ile Ile
    50                  55                  60

Pro Lys Leu Lys Glu Ile Cys Asp Ile Ser Ser Lys Leu Gly Ile Gln
65                  70                  75                  80

Ile Ile Thr Ala Phe Ala Phe Ser Thr Glu Asn Trp Lys Arg Ser Lys
                85                  90                  95

Glu Glu Val Gln Tyr Val Met Asp Leu Met Leu Glu Lys Ile Glu Gly
            100                 105                 110

Met Ile Met Glu Glu Ser Ile Ile Asn Ala Tyr Asp Ile Cys Val Ser
        115                 120                 125

Ile Ile Gly Cys Lys Ser Asp Leu Pro Met Thr Leu Gln Lys Cys Ile
    130                 135                 140

Ala Leu Thr Glu Glu Thr Thr Lys Gly Asn Lys Gly Leu His Leu Val
145                 150                 155                 160

Ile Ala Leu Asn Tyr Gly Gly Tyr Tyr Asp Ile Leu Gln Ala Thr Lys
                165                 170                 175

Ser Ile Val Asn Lys Ala Met Asn Gly Leu Leu Asp Val Glu Asp Ile
            180                 185                 190

Asn Lys Asn Leu Phe Asp Gln Glu Leu Glu Ser Lys Cys Pro Asn Pro
        195                 200                 205

Asp Leu Leu Ile Arg Thr Gly Gly Glu Gln Arg Val Ser Asn Phe Leu
    210                 215                 220

Leu Trp Gln Leu Ala Tyr Thr Glu Phe Tyr Phe Thr Asn Thr Leu Phe
225                 230                 235                 240

Pro Asp Phe Gly Glu Glu Asp Leu Lys Glu Ala Ile Met Asn Phe Gln
                245                 250                 255

Gln Arg His Arg Arg Phe Gly Gly His Thr Tyr
            260                 265
```

<210> SEQ ID NO 20
<211> LENGTH: 34
<212> TYPE: DNA
<213> ORGANISM: Artificial Sequence
<220> FEATURE:

<223> OTHER INFORMATION: PRIMER-3

<400> SEQUENCE: 20

```
tttggatccg atggaattat acaacggtga gagg                                34
```

<210> SEQ ID NO 21
<211> LENGTH: 39
<212> TYPE: DNA
<213> ORGANISM: Artificial Sequence
<220> FEATURE:
<223> OTHER INFORMATION: PRIMER-4

<400> SEQUENCE: 21

```
tttgcggccg cttattttaa gtattcctta tgtttctcc                           39
```

<210> SEQ ID NO 22
<211> LENGTH: 873
<212> TYPE: DNA
<213> ORGANISM: Hevea brasiliensis

<400> SEQUENCE: 22

```
atggaattat acaacggtga gaggccaagt gtgttcagac ttttagggaa gtatatgaga     60
aaagggttat atagcatcct aacccagggt cccatcccta ctcatattgc cttcatattg    120
gatggaaaca ggaggtttgc taagaagcat aaactgccag aaggaggtgg tcataaggct    180
ggattttttag ctcttctgaa cgtactaact tattgctatg agttaggagt gaaatatgcg    240
actatctatg cctttagcat cgataatttt cgaaggaaac ctcatgaggt tcagtacgta    300
atggatctaa tgctggagaa gattgaaggg atgatcatgg aagaaagtat catcaatgca    360
tatgatattt gcgtacgttt tgtgggtaac ctgaagcttt taagtgagcc agtcaagacc    420
gcagcagata agattatgag ggctactgcc aacaattcca aatgtgtgct tctcattgct    480
gtatgctata cttcaactga tgagatcgtg catgctgttg aagaatcctc tgaattgaac    540
tccaatgaag tttgtaacaa tcaagaattg gaggaggcaa atgcaactgg aagcggtact    600
gtgattcaaa ttgagaacat ggagtcgtat tctggaataa aacttgtaga ccttgagaaa    660
aacacctaca taaatcctta tcctgatgtt ctgattcgaa cttctgggga gacccgtctg    720
agcaactact tactttggca gactactaat tgcatactgt attctcctca tgcactgtgg    780
ccagagattg gtcttcgaca cgtggtgtgg gcagtaatta acttccaacg tcattattct    840
tacttggaga aacataagga atacttaaaa taa                                 873
```

<210> SEQ ID NO 23
<211> LENGTH: 290
<212> TYPE: PRT
<213> ORGANISM: Hevea brasiliensis

<400> SEQUENCE: 23

```
Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Arg Arg Phe Ala Lys
        35                  40                  45

Lys His Lys Leu Pro Glu Gly Gly His Lys Ala Gly Phe Leu Ala
    50                  55                  60

Leu Leu Asn Val Leu Thr Tyr Cys Tyr Glu Leu Gly Val Lys Tyr Ala
65                  70                  75                  80
```

```
Thr Ile Tyr Ala Phe Ser Ile Asp Asn Phe Arg Arg Lys Pro His Glu
                85                  90                  95

Val Gln Tyr Val Met Asp Leu Met Leu Glu Lys Ile Glu Gly Met Ile
            100                 105                 110

Met Glu Glu Ser Ile Ile Asn Ala Tyr Asp Ile Cys Val Arg Phe Val
            115                 120                 125

Gly Asn Leu Lys Leu Leu Ser Glu Pro Val Lys Thr Ala Ala Asp Lys
        130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Gly Thr Val Ile Gln Ile Glu Asn Met Glu
        195                 200                 205

Ser Tyr Ser Gly Ile Lys Leu Val Asp Leu Glu Lys Asn Thr Tyr Ile
210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

His Ala Leu Trp Pro Glu Ile Gly Leu Arg His Val Val Trp Ala Val
            260                 265                 270

Ile Asn Cys Gln Arg His Tyr Ser Tyr Leu Glu Lys His Lys Glu Tyr
            275                 280                 285

Leu Lys
    290

<210> SEQ ID NO 24
<211> LENGTH: 24
<212> TYPE: PRT
<213> ORGANISM: Hevea brasiliensis

<400> SEQUENCE: 24

Asp Leu Met Leu Glu Lys Ile Glu Gly Met Ile Met Glu Glu Ser Ile
1               5                   10                  15

Ile Asn Ala Tyr Asp Ile Cys Val
            20

<210> SEQ ID NO 25
<211> LENGTH: 60
<212> TYPE: PRT
<213> ORGANISM: Micrococcus luteus
<220> FEATURE:
<221> NAME/KEY: misc_feature
<223> OTHER INFORMATION: UDP(M.luteus B-P 26CPT)

<400> SEQUENCE: 25

Gly Val Lys Tyr Leu Thr Leu Tyr Ala Phe Ser Thr Glu Asn Trp Ser
1               5                   10                  15

Arg Pro Lys Asp Glu Val Asn Tyr Leu Met Lys Leu Pro Gly Asp Phe
            20                  25                  30

Leu Asn Thr Phe Leu Pro Glu Leu Ile Glu Lys Asn Val Lys Val Glu
        35                  40                  45

Thr Ile Gly Phe Ile Asp Asp Leu Pro Asp His Thr
    50                  55                  60
```

<210> SEQ ID NO 26
<211> LENGTH: 56
<212> TYPE: PRT
<213> ORGANISM: Unknown
<220> FEATURE:
<223> OTHER INFORMATION: NDPS (neryl diphosphate synthase)

<400> SEQUENCE: 26

Gly Ile Gln Ile Ile Thr Ala Phe Ala Phe Ser Thr Glu Asn Trp Lys
 1               5                  10                  15

Arg Ser Lys Glu Glu Val Asp Phe Leu Leu Gln Met Phe Glu Glu Ile
            20                  25                  30

Tyr Asp Glu Phe Ser Arg Ser Gly Val Arg Val Ser Ile Ile Gly Cys
        35                  40                  45

Lys Ser Asp Leu Pro Met Thr Leu
    50                  55

<210> SEQ ID NO 27
<211> LENGTH: 60
<212> TYPE: PRT
<213> ORGANISM: Arabidopsis thaliana
<220> FEATURE:
<221> NAME/KEY: misc_feature
<223> OTHER INFORMATION: AtCPT4

<400> SEQUENCE: 27

Gly Ile Gln Val Leu Thr Val Phe Ala Phe Ser Thr Asp Asn Trp Ile
 1               5                  10                  15

Arg Pro Arg Ile Glu Ile Asp Phe Leu Phe Ser Leu Phe Glu Arg Ser
            20                  25                  30

Leu Lys Thr Glu Phe Gln Asn Leu Ala Lys Asn Asn Val Arg Ile Ser
        35                  40                  45

Ile Ile Gly Asp Ser Ser Lys Leu Pro Lys Ser Leu
    50                  55                  60

<210> SEQ ID NO 28
<211> LENGTH: 59
<212> TYPE: PRT
<213> ORGANISM: Artificial Sequence
<220> FEATURE:
<223> OTHER INFORMATION: Synthetic: trNDPS1 H3AtCPT4 Chimera

<400> SEQUENCE: 28

Gly Ile Gln Ile Ile Thr Ala Phe Ala Phe Ser Thr Glu Asn Trp Lys
 1               5                  10                  15

Arg Ser Lys Glu Glu Val Asp Phe Leu Leu Ser Leu Phe Glu Arg Ser
            20                  25                  30

Leu Lys Thr Glu Phe Gln Asn Leu Ala Lys Asn Asn Val Arg Ile Ile
        35                  40                  45

Ile Gly Cys Lys Ser Asp Leu Pro Met Thr Leu
    50                  55

<210> SEQ ID NO 29
<211> LENGTH: 55
<212> TYPE: PRT
<213> ORGANISM: Micrococcus luteus
<220> FEATURE:
<221> NAME/KEY: misc_feature
<223> OTHER INFORMATION: UDP (M. luteus B-P 26CPT)

<400> SEQUENCE: 29

Thr Glu Asn Trp Ser Arg Pro Lys Asp Glu Val Asn Tyr Leu Met Lys

```
                1               5                    10                   15
Leu Pro Gly Asp Phe Leu Asn Thr Phe Leu Pro Glu Leu Ile Glu Lys
                    20                  25                  30

Asn Val Lys Val Glu Thr Ile Gly Phe Ile Asp Asp Leu Pro Asp His
                    35                  40                  45

Thr Lys Lys Ala Val Leu Glu
                50                  55

<210> SEQ ID NO 30
<211> LENGTH: 55
<212> TYPE: PRT
<213> ORGANISM: Escherichia coli
<220> FEATURE:
<221> NAME/KEY: misc_feature
<223> OTHER INFORMATION: UPPS (Escherichia coli)

<400> SEQUENCE: 30

Ser Glu Asn Trp Asn Arg Pro Ala Gln Glu Val Ser Ala Leu Met Glu
1               5                   10                  15

Leu Phe Val Trp Ala Leu Asp Ser Glu Val Lys Ser Leu His Arg His
                    20                  25                  30

Asn Val Arg Leu Arg Ile Ile Gly Asp Thr Ser Arg Phe Asn Ser Arg
                    35                  40                  45

Leu Gln Glu Arg Ile Arg Lys
                50                  55

<210> SEQ ID NO 31
<211> LENGTH: 60
<212> TYPE: PRT
<213> ORGANISM: Saccharomyces cerevisiae
<220> FEATURE:
<221> NAME/KEY: misc_feature
<223> OTHER INFORMATION: Srt1 (Yeast CPT)

<400> SEQUENCE: 31

Ile Glu Asn Phe Asn Arg Pro Lys Glu Val Asp Thr Leu Met Asn
1               5                   10                  15

Leu Phe Thr Val Lys Leu Asp Glu Phe Ala Lys Arg Ala Lys Asp Tyr
                    20                  25                  30

Lys Asp Pro Leu Tyr Gly Ser Lys Ile Arg Ile Val Gly Asp Gln Ser
                    35                  40                  45

Leu Leu Ser Pro Glu Met Arg Lys Lys Ile Lys Lys
                50                  55                  60

<210> SEQ ID NO 32
<211> LENGTH: 58
<212> TYPE: PRT
<213> ORGANISM: Homo sapiens
<220> FEATURE:
<221> NAME/KEY: misc_feature
<223> OTHER INFORMATION: HDS (Human CPT)

<400> SEQUENCE: 32

Ile Glu Asn Phe Lys Arg Ser Lys Ser Glu Val Asp Gly Leu Met Asp
1               5                   10                  15

Leu Ala Arg Gln Lys Phe Ser Arg Leu Met Glu Glu Lys Glu Lys Leu
                    20                  25                  30
```

-continued

```
Gln Lys His Gly Val Cys Ile Arg Val Leu Gly Asp Leu His Leu Leu
        35                  40                  45

Pro Leu Asp Leu Gln Glu Leu Ile Ala Gln
        50                  55
```